United States Patent
Moss

(10) Patent No.: US 6,737,066 B1
(45) Date of Patent: May 18, 2004

(54) HIV IMMUNOGENIC COMPOSITIONS AND METHODS

(75) Inventor: Ronald B. Moss, San Diego, CA (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

(21) Appl. No.: 09/565,906

(22) Filed: May 5, 2000

Related U.S. Application Data
(60) Provisional application No. 60/150,667, filed on Aug. 25, 1999, and provisional application No. 60/132,762, filed on May 6, 1999.

(51) Int. Cl.$^7$ ............................................. A61K 39/21
(52) U.S. Cl. ............................. 424/208.1; 424/188.1; 424/278.1; 536/24.1
(58) Field of Search ........................... 435/5; 424/188.1, 424/208.1, 278.1

(56) References Cited

U.S. PATENT DOCUMENTS

| | | | | |
|---|---|---|---|---|
| 5,256,767 A | | 10/1993 | Salk et al. ................... | 530/350 |
| 5,759,769 A | * | 6/1998 | Sia et al. ....................... | 435/5 |

FOREIGN PATENT DOCUMENTS

| | | | | |
|---|---|---|---|---|
| WO | WO 98/16247 | * | 4/1998 | |
| WO | WO 98/40100 | | 9/1998 | |
| WO | WO 98/55495 | | 12/1998 | ........... C07H/21/00 |
| WO | WO 99/62923 | | 12/1999 | ........... C07H/21/00 |
| WO | WO 00/21556 | | 4/2000 | .......... A61K/39/21 |
| WO | WO 01/72123 | | 10/2001 | |

OTHER PUBLICATIONS

US 6,008,200, 12/1999, Krieg (withdrawn)
Moss et al., "Tumor necrosis factor alpha and human immunodefiency virus –specific functional immune responses after immunization with Gp120—depleted, inactivated HIV –1 in incomplete Freund's adjuvant (REMUNE) in HIV –1–seropositive subjects." *J. Hum. Virol.* 1(2): 77–81 (1998).
Sun et al., "DNA as an adjuvant: capacity of insect DNA and synthetic oligodeoxynucleotides to augment T cell responses to specific antigen," *J. Exp. Med.* 187(7): 1145–1150 (1998).
Annunziato et al., "Limited expression of R5–topic HIV–1 in CCR5–positive type 1–polarized T cells explained by their ability to produce RANTES, MIP–1α, and MIP–1β" *Blood*, 95:1167–1174 (2000).
Asakura et al., "Th1–biased immune responses induced by DNA–based immunizations are mediated via action on professional antigen–presenting cells to up–regulate IL–12 production" *Clin. Exp. Immunol.*, 119:130–139 (2000).
Cho et al., "Immunostimulatory DNA–based vaccines induce cytotoxic lymphocyte activity by a T–helper cell–1–independent mechanism" *Nature Biotechnology*, 18:509–514 (2000).
Cocchi et al., "Identification of RANTES, MIP–1α, and MIP–1β as the major HIV–suppressive factors produced by CD8$^+$ T cells" *Science*, 270: 1811–1815 (1995).
Davis et al., "CpG DNA overcomes hyporesponsiveness to hepatitis B vaccine in orangutans" *Vaccine*, 18:1920–1924 (2000).
Demi et al., "Immunostimulatory CpG motifs trigger a T helper–1 immune response to human immunodeficiency virus type–1 (HIV–1) gp160 envelope proteins" *Clin. Chem. Lab Med.*, 37:199–204 (1999).
Fransen et al., "RANTES production by T cells and CD8–Mediated Inhibition of human immunodeficiency virus gene expression before initiation of potent antiretroviral therapy predict sustained suppression of viral replication" *J. Infect. Diseases*, 181:505–512 (2000).
Girard et al., "New prospects for the development of a vaccine against human immunodeficiency virus type 1. An overview" *C.R. Acad. Sci. Paris, Sciences de la vie*, 322:959–966 (1999).
Hartmann et al., "Delineation of a CpG phosphorothioate oligodeoxynucleotide for activating primate immune reponses in vitro and in vivo" *J. of Immunol.*, 164:1617–1624 (2000).
Kalinkovich et al., "Chemokines and chemokine receptors: role in HIV infection" *Immunology Letters*, 68:281–287 (1999).
Klinman et al., "CpG motifs as immune adjuvants" *Vaccine*, 17:19–25 (1999).

(List continued on next page.)

Primary Examiner—James Housel
Assistant Examiner—Jeffrey S. Parkin
(74) Attorney, Agent, or Firm—McDermott, Will & Emery

(57) ABSTRACT

The invention provides immunogenic compositions which enhance β-chemokine levels in a mammal. The immunogenic compositions contain an HIV antigen, an isolated nucleic acid molecule containing an immunostimulatory sequence (ISS) and an adjuvant. The HIV antigen can be a whole-killed HIV virus devoid of outer envelope protein gp120. Alternatively, the HIV antigen can be a whole-killed HIV virus, or a p24 antigen. Also provided are kits, the components of which, when combined, produce the immunogenic compositions of the invention. The invention also provides methods of making the immunogenic compositions, by combining an HIV antigen, an isolated nucleic acid molecule containing an immunostimulatory sequence (ISS) and an adjuvant. The invention further provides a method of immunizing a mammal, by enhancing β-chemokine production in the mammal by administering to the mammal an immunogenic composition containing an HIV antigen, an isolated nucleic acid molecule containing an immunostimulatory sequence (ISS) and an adjuvant. Also provided is a method of inhibiting AIDS, by enhancing β-chemokine production in the mammal by administering to the mammal an immunogenic composition containing an HIV antigen, an isolated nucleic acid molecule containing an immunostimulatory sequence (ISS) and an adjuvant.

24 Claims, 15 Drawing Sheets

OTHER PUBLICATIONS

Lanza et al., "Whole–killed gp120–depleted HIV–1 antigen in a murine model for prophylactic vaccination" *Vaccine*, 16:727–731 (1998).

Lebner et al., "A rational basis for mucosal vaccination against HIV infection" *Immunological Reviews*, 170:183–196 (1999).

Maeda et al., "Acquisition of HIV type 1 resistance by β–chemokine–producing CD4$^+$ T cells" *Aids Research and Human Retroviruses*, 15:1453–1460 (1999).

Moldoveanu et al., "CpG DNA, a novel immune enhancer for systemic and mucosal immunization with influenza virus" *Vaccine*, 16:1216–1224 (1998).

Moss et al., "Effect of immunization with an inactivated gp120–depleted HIV–1 immunogen on β–chemokine and cytokine production in subjects with HIV–1 infection" *J. of Acquired Immune Deficiency Synd. And Human Retrovirology*, 14:343–350 (1997).

Moss et al., "In vitro immune function after vaccination with an inactivated, gp120–depleted HIV–1 antigen with immunostimulatory oligodeoxynucleotides" *Vaccine*, 18:1081–1087 (2000).

Moss et al., "A primer on HIV type 1–specific immune function and remune™", *Aids Research and Human Retroviruses*, 14:S167–S175 (1998).

Pisetsky, David S., "Immunostimulatory DNA: A clear and present danger?" *Nature Medicine*, 3:829–831 (1997).

Roman et al., "Immunostimulatory DNA sequences function as T helper–1 promoting adjuvants" *Nature Medicine*, 3:849–854 (1997).

Salmon–Céron, et al., "Safety and immunogenicity of a live recombinant canarypox virus expressing HIV type 1 gp120 MN tm/gag/protease LAI (ALAVAC–HIV, v CP205) followed by a p24E–V3 MN synthetic peptide (CLTB–36) administered in healthy volunteers at low risk for HIV infection" *Aids Research and Human Retroviruses*, 15:633–645 (1999).

Vogel, Frederick R., "The role of adjuvants in retroviral vaccines" *Int. J. Immunopharmac.*, 17:85–90 (1995).

Weiner et al., "Immunostimulatory oligodeoxynucleotides containing the CpG motif are effective as immune adjuvants in tumor antigen immunization" *Proc. Natl. Acad. Sci. USA*, 94:10833–10837 (1997).

Ylisastigui et al., "Effect of RANTES on the infection of monocyte–derived primary macrophages by human immunodeficiency virus type 1 and type 2" *Biomed & Pharmacother*, 52:447–453 (1998).

Zajac et al., "Therapeutic vaccination against chronic viral infection: the importance of cooperation between CD4$^+$ and CD8$^+$ T cells" *Current Opinion in Immunology*, 10:444–449 (1998).

Zhao et al., "Site of chemical modifications in CpG containing phosphorothioate oligodeoxynucleotide modulates its immunostimulatory activity" *Bioorganic & Med. Chem. Letters*, 9:3453–3458 (1999).

Davis, H., et al., "CpG DNA is a potent enhancer of specific immunity in mice immunized with recombinant hepatitis B surface antigen.", J. Immunol., (Jan. 15, 1998) 160(2):870–6.*

Moss, R. B., et al., "Effect of immunization with an inactivated gp120–depleted HIV–1 immunogen on β–chemokine and cytokine production in subjects with HIV–1 infection.", J. Acquir. Immune Defic. Syndr. Human Retrovir., (1997) 14:343–350.*

Roman, M., et al., "Immunostimulatory DNA sequences function as T helper–1–promoting adjuvants.", Nature Med., (Aug. 1997) 3(8):849–854.*

Rickman, L. S., et al., "Use of adjuvant containing mycobacterial cell–wall skeleton, monophosphoryl lipid A, and squalane in malaria circumsporozoite protein vaccine.", Lancet, (Apr. 27, 1991) 337(8748):998–1001.*

Chu et al., "CpG Oligodeoxynucleotides Act as Adjuvants that Switch on T Helper 1 (Th1) Immunity," *J. Exp. Med.* 186:1623–1631 (1997).

Davis, "DNA Vaccines for Prophylactic or Therapeutic Immunization Against Hepatitis B Virus," *Grand Rounds* 66:84–90 (1999).

Ferrari et al., "Clade B–based HIV–1 vaccines elicit cross–clade cytotoxic T lymphocyte reactivities in uninfected volunteers," *Proc. Natl. Acad. Sci. USA* 94:1396–1401 (1997).

Garzino–Demo et al., "β–Chemokines and Protection from HIV Type 1 Disease," *Aids Res. Hum. Ret.* 14:S–177—S–184 (1998).

Handen and Rosenberg, "Suppression of HIV–1 transcription by β–chemokines RANTES, MIP–α, and MIP–1β is not mediated by the NFAT–1 enhancer element," *FEBS Letters* 410:301–302 (1997).

Heeney et al., "β–Chemokines and neutralizing antibody titers correlate with sterilizing immunity generated in HIV–1 vaccinated macaques," *Proc. Natl. Acad. Sci. USA* 95:10803–10808 (1998).

Heeney et al., "HIV–1 vaccine–induced immune responses which correlate with protection from SHIV infection: compiled preclinical efficacy data from trials with ten different HIV–1 vaccine candidates," *Immunology Letters* 66:189–195 (1999).

Horner et al., "Immunostimulatory DNA–Based Vaccines Elicit Multifaceted Immune Responses Against HIV at Systemic and Mucosal Sites[1]," *The Journal of Immunology* 167:1584–1591 (2001).

Lanza et al., "Whole–killed gp120–depleted HIV–1 antigen in a murine model for prophylactic vaccination," *Vaccine* 16: 727–731 (1998).

Lee and Sung, "Immuno–stimulatory effects of bacterial–derived plasmids depend on the nature of the antigen to intramuscular DNA inoculations," *Immunology* 94:285–289 (1998).

Lehner et al., "A rational basis for mucosal vaccination against HIV infection," *Immunological Reviews* 170:183–196 (1999).

Leitner et al., "DNA and RNA–based vaccines: principles, progress and prospects," *Vaccine* 18:765–777 (2000).

Letvin, "Progress in the Development of an HIV–1 Vaccine," *Science* 280:1875–1880 (1998).

Manders and Thomas, "Immunology of DNA vaccines: CpG motifs and antigen presentation," *Inflamm. Res.* 49:199–205 (2000).

Moldoveanu et al., "CpG DNA, a novel immune enhancer for systemic and mucosal immunization with influenza virus," *Vaccine* 16:1216–1224 (1998).

Moss et al., "In Vitro p24 Antigen–Stimulated Lymphocyte Proliferation and β–Chemokine Production in Human Immunodeficiency Virus Type 1 (HIV–1)–Seropositive Subjects after Immunization with an Inactivated gp120–Depleted HIV–1 Immunogen (Remune)," *Clin. And Diag. Lab. Immun.* 5:308–312 (1998).

Moss et al., "In vitro immune function after vaccination with an inactivated, gp120–depleted HIV–1 antigen with immunostimulatory oligodeoxynucleotides," *Vaccine* 18:1081–1087 (2000).

Murthy et al., "Correlates of protective immunity against HIV–1 infection in immunized chimpanzees," *Immunology Letters* 51:121–124 (1996).

Rickman et al., "Use of adjuvant containing mycobacterial cell–wall skeleton, monophosphoryl lipid A, and squalane in malaria circumsporozoite protein vaccine," *The Lancet* 337:998–1001 (1991).

Roman et al., "Immunostimulatory DNA sequences function as T helper–1–promoting adjuvants," *Nature Medicine* 3:849–854 (1997).

Stan et al., "CpG motifs of DNA vaccines induce the expression of chemokines and MHC class II molecules on myocytes," *Eur. J. Immunology* 31:301–310 (2001).

Takeshita et al., "CpG Oligodeoxynucleotides Induce Murine Macrophages to Up–Regulate Chemokine mRNA Expression," *Cellular Immunology* 206:101–106 (2000).

Tascon et al., "Immunostimulatory bacterial DNA sequences activate dendritic cells and promote priming and differentiation of $CD8^+$ T cells," *Immunology* 99:1–7 (2000).

Van De Wijgert et al., "Immunogenicity of *Streptococcus pneumoniae* Type 14 Capsular Polysaccharide: Influence of Carriers and Adjuvants on Isotype Distribution," *Infection And Immunity* 59:2750–2757 (1991).

Wagner et al., "β–Chemokines are released from HIV–1–specific cytolytic T–cell granules complexed to proteoglycans," *Nature* 391:908–911 (1998).

Xu et al., "Identification of a New Member of the MNP Transcription Factor Family in Differentiated HL60 Cells," *Biochem. And Biophys. Res. Comm.* 226:488–494 (1996).

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: phosphorothioate-modified synthetic
      oligodeoxynucleotide

<400> SEQUENCE: 1
tccatgacgt tcctgacgtt                                          20

<210> SEQ ID NO 2
<211> LENGTH: 22
<212> TYPE: DNA
<213> ORGANISM: Artificial Sequence
<220> FEATURE:
<223> OTHER INFORMATION: phosphorothioate-modified synthetic
      oligodeoxynucleotide

<400> SEQUENCE: 2
tgactgtgaa cgttcgagat ga                                       22

<210> SEQ ID NO 3
<211> LENGTH: 21
<212> TYPE: DNA
<213> ORGANISM: Artificial Sequence
<220> FEATURE:
<223> OTHER INFORMATION: phosphorothioate-modified synthetic
      oligodeoxynucleotide

<400> SEQUENCE: 3
tccaatgagc ttcctgagtc t                                        21

<210> SEQ ID NO 4
<211> LENGTH: 21
<212> TYPE: DNA

-continued

```
<213> ORGANISM: Artificial Sequence
<220> FEATURE:
<223> OTHER INFORMATION: phosphorothioate-modified synthetic
      oligodeoxynucleotide

<400> SEQUENCE: 4
tcgtcgctgt tgtcgtttct t                                      21
```

HIV IMMUNOGENIC COMPOSITIONS AND METHODS

This application claims priority to U.S. provisional applications 60/132,762, filed May 6, 1999, and 60/150,667, filed Aug. 25, 1999. The contents of these applications are incorporated herein by reference in their entirety.

BACKGROUND INFORMATION

This invention relates to Acquired Immunodeficiency Syndrome (AIDS) and, more specifically, to immunogenic compositions for use in preventing and treating AIDS.

More than 30 million people world wide are now infected with the human immunodeficiency virus (HIV), the virus responsible for AIDS. About 90% of HIV infected individuals live in developing countries, including sub-Saharan Africa and parts of South-East Asia, although the HIV epidemic is rapidly spreading throughout the world. Antiviral therapeutic drugs that reduce viral burden and slow the progression to AIDS have recently become available. However, these drugs are prohibitively expensive for use in developing nations. Thus, there remains an urgent need to develop effective preventative and therapeutic vaccines to curtail the global AIDS epidemic.

To date, HIV has proven a difficult target for effective vaccine development. Because of the propensity of HIV to rapidly mutate, there are now numerous strains predominating in different parts of the world whose epitopes differ. Additionally, in a particular infected individual, an HIV virus can escape from the control of the host immune system by developing mutations in an epitope. There remains a need to develop improved HIV vaccines that stimulate the immune system to recognize a broad spectrum of conserved epitopes, including epitopes from the p24 core antigen.

During the 1990's, more than 30 different candidate HIV-1 vaccines entered human clinical trials. These vaccines elicit various humoral and cellular immune responses, which differ in type and strength depending on the particular vaccine components. There remains a need to develop HIV vaccine compositions that strongly elicit the particular immune responses correlated with protection against HIV infection.

The nature of protective HIV immune responses has been addressed through studies of individuals who have remained uninfected despite repeated exposure to HIV, or who have been infected with HIV for many years without developing AIDS. These studies have shown that immune responses of the T helper 1 (Th1) type correlate well with protection against HIV infection and subsequent disease progression. Besides antigen-specific Th1 responses, CD8+ cytotoxic T cell responses are considered important in preventing initial HIV infection and disease progression. During an effective anti-viral immune response, activated CD8+ T cells directly kill virus-infected cells and secrete cytokines with antiviral activity.

The β-chemokine system also appears to be important in protection against initial HIV infection and disease progression. Infection of immune cells by most primary isolates of HIV requires interaction of the virus with CCR5, whose normal biological role is as the principal receptor for the β-chemokines RANTES, MIP-1α and MIP-β. Genetic polymorphisms resulting in decreased expression of the CCR5 receptor have been shown to provide resistance to HIV infection. Additionally, a significant correlation between β-chemokine levels and resistance to HIV infection, both in exposed individuals and in cultured cells, has been demonstrated. It has been suggested that β-chemokines may block HIV infectivity by several mechanisms, including competing with or interfering with HIV binding to CCR5, and downregulating surface CCR5.

Because of the importance of β-chemokines in preventing initial HIV infection and disease progression, an effective HIV immunogenic composition should induce high levels of β-chemokine production, both prior to infection and in response to infectious virus. However, HIV immunogenic compositions capable of inducing high levels of β-chemokine production have not been described. In particular, immunogenic compositions which stimulate high levels of β-chemokine production, induce HIV-specific Th1 cellular and humoral immune responses, and induce HIV-specific cytotoxic activity, have not been described.

Compositions that elicit certain types of HIV-specific immune responses may not elicit other important protective responses. For example, Deml et al., *Clin. Chem. Lab. Med.* 37:199–204 (1999), describes a vaccine containing an HIV-1 gp160 envelope antigen, an immunostimulatory DNA sequence and alum adjuvant, which, despite inducing an antigen-specific Th1-type cytokine response, was incapable of inducing an antigen-specific cytotoxic T lymphocyte response. Furthermore, a vaccine containing only envelope antigens would not be expected to induce an immune response against the more highly conserved core proteins of HIV.

Thus, there exists a need for immunogenic compositions and methods that will prevent HIV infection as well as slow progression to AIDS in infected individuals. Ideally, such compositions and methods will elicit potent Th1 cellular and humoral immune responses specific for conserved HIV epitopes, elicit HIV-specific cytotoxic T lymphocyte activity, and stimulate production of high levels of β-chemokines. Such vaccines could be used to prevent maternal transmission of HIV, for vaccination of newborns, children and high-risk individuals, and for vaccination of infected individuals. Such vaccines could also be used in combination with other HIV therapies, including protease inhibitors. The present invention satisfies this need and provides related advantages as well.

SUMMARY OF THE INVENTION

The invention provides immunogenic compositions which enhance β-chemokine levels in a mammal. The immunogenic compositions contain an HIV antigen, an isolated nucleic acid molecule containing an immunostimulatory sequence (ISS) and an adjuvant. The HIV antigen can be a whole-killed HIV virus devoid of outer envelope protein gp120. Alternatively, the HIV antigen can be a whole-killed HIV virus, or a p24 antigen.

In the immunogenic compositions of the invention, the isolated nucleic acid molecule containing an ISS can be an oligodeoxynucleotide. The isolated nucleic acid molecule containing an ISS can contain two or more CpG sequences. Exemplary ISS-containing nucleic acid molecules contain the motif 5'-Cytosine, Guanine, Pyrimidine, Pyrimidine-3'. The isolated nucleic acid molecule can contain a phosphorothioate backbone. The isolated nucleic acid molecule can be conjugated to the HIV antigen.

In the immunogenic compositions of the invention, the adjuvant can be suitable for administration to a human. An exemplary adjuvant is Incomplete Freund's Adjuvant.

The immunogenic compositions of the invention can further enhance HIV-specific IgG2b antibody production in a mammal. The immunogenic compositions of the invention can also enhance an HIV-specific cytotoxic T lymphocyte response in a mammal.

Also provided are kits, which contain an HIV antigen, an isolated nucleic acid molecule containing an immunostimulatory sequence (ISS) and an adjuvant. The components of the kits, when combined, produce the immunogenic compositions of the invention.

The invention also provides methods of making the immunogenic compositions, by combining an HIV antigen, an isolated nucleic acid molecule containing an immunostimulatory sequence (ISS) and an adjuvant. The components can be combined ex vivo or in vivo to arrive at the immunogenic compositions.

The invention also provides a method of immunizing a mammal, by enhancing β-chemokine production in the mammal by administering to the mammal an immunogenic composition containing an HIV antigen, an isolated nucleic acid molecule containing an immunostimulatory sequence (ISS) and an adjuvant. Also provided is a method of inhibiting AIDS, by enhancing β-chemokine production in the mammal by administering to the mammal an immunogenic composition containing an HIV antigen, an isolated nucleic acid molecule containing an immunostimulatory sequence (ISS) and an adjuvant. In the methods of the invention, the mammal can be a primate, such as a human, or a rodent. In certain embodiments of the method, the primate is a pregnant mother or an infant. A human can be HIV seronegative or HIV seropositive. The immunogenic compositions can advantageously be administered to the mammal two or more times.

DETAILED DESCRIPTION OF THE INVENTION

Figure 1A:
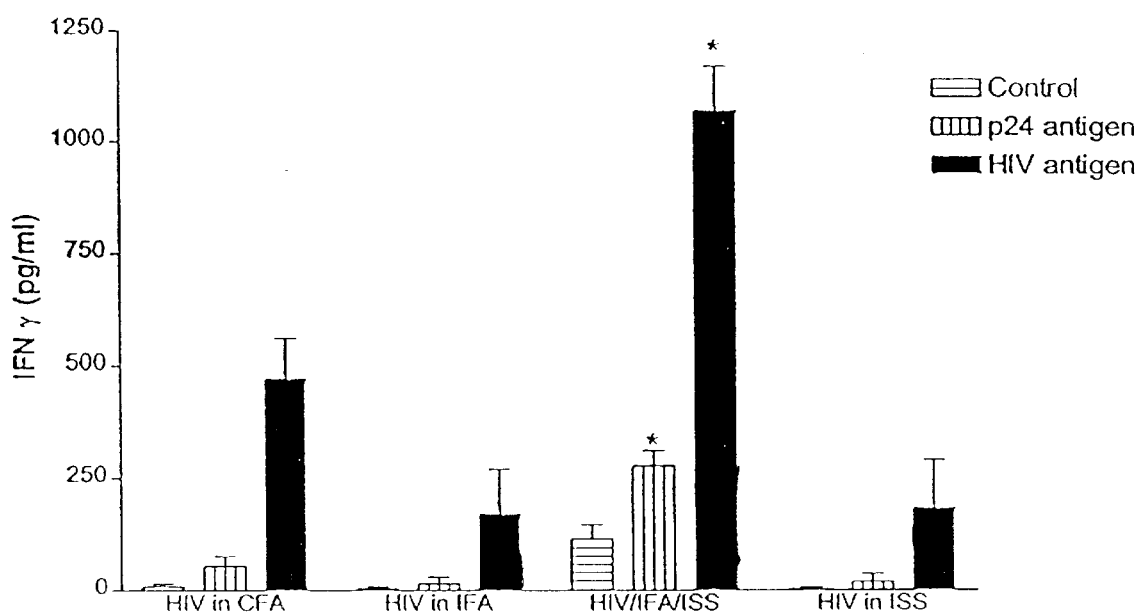
FIGS. 1A and 1B show control and antigen-stimulated interferon-γ (IFN-γ) production for indicated treatment groups.

The present invention provides immunogenic HIV compositions containing an HIV antigen, an isolated nucleic acid molecule containing an immunostimulatory sequence, and an adjuvant. Also provided are kits containing the components of such compositions, for use together. The invention also provides methods of immunizing a mammal with such compositions, or with the components of such compositions, so as to enhance production of β-chemokines in the immunized mammal. Advantageously, the compositions of the invention can also induce potent Th1 immune responses against a broad spectrum of HIV epitopes, and provide a strong HIV-specific cytotoxic T lymphocyte response. Thus, the immunogenic compositions of the invention are useful for preventing HIV infection and slowing progression to AIDS in infected individuals.

As used herein, the term "HIV" refers to all forms, subtypes and variations of the HIV virus, and is synonymous with the older terms HTLVIII and LAV. Various cell lines permanently infected with the HIV virus have *been developed and deposited with the ATCC, including those having accession numbers CCL 214, TIB 161, CRL 1552 and CRL 8543, all of which are described in U.S. Pat. No. 4,725,669 and Gallo, *Scientific American* 256:46 (1987).

As used he,rein, the term "whole-killed HIV virus" refers to an intact, inactivated HIV virus.

As used herein, the term "outer envelope protein" refers to that portion of the membrane glycoprotein of a retrovirus which protrudes beyond the membrane, as opposed to the transmembrane protein, gp41.

As used herein, the term "HIV virus devoid of outer envelope proteins" refers to a preparation of HIV particles or HIV gene products devoid of the outer envelope protein gp120, but: contains the more genetically conserved parts of the virus (eg. p24 and gp41).

As used herein, the term "HIV p24 antigen" refers to the gene product of the gag region of HIV, characterized as having an apparent relative molecular weight of about 24,000 daltons designated p24. The term "HIV p24 antigen" also refers to modifications and fragments of p24 having the immunological activity of p24. Those skilled in the art can determine appropriate modifications of p24, such as additions, deletions or substitutions of natural amino acids or amino acid analogs, that serve, for example, to increase its stability or bioavailability or facilitate its purification, without destroying its immunological activity. Likewise, those skilled in the art can determine appropriate fragments of p24 having the immunological activity of p24. An immunologically active fragment of p24 can have from 6 residues from the polypeptide up to the full length polypeptide minus one amino acid.

As used herein, the term "immunostimulatory sequence" or "ISS" refers to a nucleotide sequence containing an unmethylated CpG motif that is capable of enhancing the immune response in a mammal when administered in combination with an antigen. Immunostimulatory sequences are described, for example, in PCT publication WO 98/55495.

As ISS can contain, for example, at least one sequence consisting of 5'-Cytosine, Guanine, Pyrimidine, Pyrimidine-3'. For example, the sequence 5'-CGTT-3' is found in two copies in the sequence designated SEQ ID NO:1, described in Example I, and one copy each of the sequence 5'-CGTT-3' and the sequence 5'-CGCT-3' are found in the sequence designated SEQ ID NO:4, described in Example IV.

An ISS can contain the hexameric motif 5'-Purine, Purine, Cytosine, Guanine, Pyrimidine, Pyrimidine-3', such as the motif 5'-GACGTT-3', two copies of which are found in the nucleotide sequence designated SEQ ID NO:1. An ISS can also contain, for example, either the octameric motif 5'-Purine, Purine, Cytosine, Guanine, Pyrimidine, Pyrimidine, Cytosine, Cytosine-3' or 5'-Purine, Purine, Cytosine, Guanine, Pyrimidine, Pyrimidine, Cytosine, Guanine-3', such as the sequence 5'-AACGTTCG-3'. An exemplary isolated nucleic acid molecule containing the ISS motif 5'-AACGTTCG -3' has the nucleotide sequence designated SEQ ID NO:2, as described in Example I.

An ISS can contain more than one unmethylated CpG motif, such as two or more CpG motifs. An exemplary isolated nucleic acid molecule containing two CpG motifs has the nucleotide sequence designated SEQ ID NO:1 or the sequence designated SEQ ID NO:2, described in Example I, below. An exemplary isolated nucleic acid molecule containing three unmethylated CpG motifs has the nucleotide sequence designated SEQ ID NO:4, as described in Example IV. SEQ ID NO:4 also contains two copies of the hexameric motif 5'-Purine, Pyrimidine, Cytosine, Guanine, Pyrimidine, Pyrimidine-3', namely both the sequence 5'-GTCGCT-3' and the sequence 5'-GTCGTT-3'.

As used herein, the term "nucleic acid molecule containing an ISS" refers to a linear, circular or branched single- or double-stranded DNA or RNA nucleic acid that contains an immunostimulatory sequence. The term "isolated," with reference to a nucleic acid molecule containing an ISS, is intended to distinguish the ISS-containing nucleic acid molecule from an ISS that may naturally be present in a whole-killed HIV virus preparation. A nucleic acid molecule containing an ISS can contain multiple ISSs. The ISSs can be adjacent within the nucleic acid molecule, or they can be separated by additional nucleotide bases within the nucleic acid molecule. Such a nucleic acid molecule can be of any length greater than 6 bases or base pairs, and is preferably greater than about 15 bases or base pairs, such as greater than about 20 bases or base pairs, and can be several kb in length.

A nucleic acid molecule containing an ISS can be, for example, a synthetic oligonucleotide, a naturally occurring nucleic acid molecule of any species, or a vector. A nucleic acid molecule containing an ISS can contain either natural or modified nucleotides or natural or unnatural nucleotide linkages. Modifications known in the art, include, for example, modifications of the 3'OH or 5'OH group, modifications of the nucleotide base, modifications of the sugar component, and modifications of the phosphate group. An unnatural nucleotide linkage can be, for example, a phosphorothioate linkage in place of a phosphodiester linkage, which increases the resistance of the nucleic acid molecule to nuclease degradation. Various modifications and linkages are described, for example, in PCT publication WO 98/55495.

As used herein, the term "adjuvant" refers to a substance which, when added to an immunogenic agent, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as polysytrene, starch, polyphosphazene and polylactide/polyglycosides. Adjuvants can also include, for example, squalene mixtures (SAF-I), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant (both complete and incomplete) can be used. In humans, Incomplete Freund's Adjuvant (IFA) is a preferred adjuvant. Various appropriate adjuvants are well known in the art and are reviewed, for example, by Warren and Chedid, *CRC Critical Reviews in Immunology* 8:83 (1988).

As used herein, "AIDS" refers to the symptomatic phase of HIV infection, and includes both Acquired Immune Deficiency Syndrome (commonly known as AIDS) and "ARC," or AIDS-Related Complex, as described by Adler, *Brit. Med. J.* 294: 1145 (1987). The immunological and clinical manifestations of AIDS are well known in the art and include, for example, opportunistic infections and cancers resulting from immune deficiency.

As used herein, the term "inhibiting AIDS" refers to a beneficial prophylactic or therapeutic effect of the immunogenic composition in relation to HIV infection or AIDS symptoms. Such beneficial effects include, for example, preventing initial infection of an individual exposed to HIV; reducing viral burden in an individual infected with HIV; prolonging the asymptomatic phase of HIV infection; increasing overall health or quality of life in an individual with AIDS; and prolonging life expectency of an individual with AIDS. A clinician can compare the effect of immunization with the patient's condition prior to treatment, or with the expected condition of an untreated patient, to determine whether the treatment is effective in inhibiting AIDS.

As used herein, the term "β-chemokine" refers to a member of a class of small, chemoattractive polypeptides that includes RANTES, macrophage inflammatory protein-1β (MIP-1β) and macrophage inflammatory protein-1α (MIP-1α). The physical and functional properties of β-chemokines are well known in the art.

As used herein, the term "enhances," with respect to an immune response such as β-chemokine production, IgG2b production or cytotoxic T lymphocyte activity, is intended to mean that the immunogenic composition elicits a greater immune response than does a composition containing any two of the three components of the immunogenic composition, administered in the same amounts and following the same immunization schedule. As disclosed herein, the components of the immunogenic compositions of the invention can act in synergy. For example, the immunogenic compositions of the invention can enhance β-chemokine production by eliciting production of a higher concentration of β-chemokine than would be expected by adding the effects of pairwise combinations of components of the immunogenic composition.

The β-chemokine production that is enhanced can be either "HIV-specific β-chemokine production," which refers to production of a β-chemokine in response to stimulation of T cells with an HIV antigen. Alternatively, or additionally, the β-chemokine production that is enhanced can be "non-specific β-chemokine production," which refers to production of a β-chemokine in the absence of stimulation of T cells with an HIV antigen.

As used herein, the term "kit" refers to components packaged or marked for use together. For example, a kit can contain an HIV antigen, an ISS and an adjuvant in three separate containers. Alternatively, a kit can contain any two components in one container, and a third component and any additional components in one or more separate containers.

Optionally, a kit further contains instructions for combining the components so as to formulate an immunogenic composition suitable for administration to a mammal.

The invention provides an immunogenic composition containing an HIV antigen, a nucleic acid molecule containing a immunostimulatory sequence (ISS), and an adjuvant. The immunogenic composition enhances β-chemokine production in a mammal administered the composition.

In one embodiment, the HIV antigen in the immunogenic composition is a whole-killed HIV virus, which can be prepared by methods known in the art. For example, HIV virus can be prepared by culture from a specimen of peripheral blood of infected individuals. In an exemplary method of culturing HIV virus, mononuclear cells from peripheral blood (e.g. lymphocytes) can be obtained by layering a specimen of heparinized venous blood over a Ficoll-Hypaque density gradient and centrifuging the specimen. The mononuclear cells are then collected, activated, as with phytohemagglutinin for two to three days, and cultured in an appropriate medium, preferably supplemented with interleukin 2. The virus can be detected either by an assay for reverse transcriptase, by an antigen capture assay for p24, by immunofluorescence or by electron microscopy to detect the presence of viral particles in cells, all of which are methods well-known to those skilled in the art.

Methods for isolating whole-killed HIV particles are described, for example, in Richieri et al., *Vaccine* 16:119–129 (1998), and U.S. Pat. Nos. 5,661,023 and 5,256,767. In one embodiment, the HIV virus is an HZ321 isolate from an individual infected in Zaire in 1976, which is described in Choi et al., *AIDS Res. Hum. Retroviruses* 13:357–361 (1997).

Various methods are known in the art for rendering a virus non-infectious (see, for example Hanson, MEDICAL VIROLOGY II (1983), de la Maza and Peterson, eds., Elsevier,). For example, the virus can be inactivated by treatment with chemicals or by physical conditions such as heat or irradiation. Preferably, the virus is treated with an agent or agents that maintain the immunogenic properties of the virus. For example, the virus can be treated with beta-propiolactone or gamma radiation, or both beta-propiolactone and gamma radiation, at dosages and for times sufficient to inactivate the virus.

In another, embodiment, the HIV antigen in the immunogenic composition is a whole-killed HIV virus devoid of outer envelope proteins, which can be prepared by methods known in the art. In order to prepare whole-killed virus devoid of outer envelope proteins, the isolated virus is treated so as to remove the outer envelope proteins. Such removal is preferably accomplished by repeated freezing and thawing of the virus in conjunction with physical methods which cause the swelling and contraction of the viral particles, although other physical or non-physical methods, such as sonication, can also be employed alone or in combination.

In yet another embodiment, the HIV antigen in the immunogenic composition is a substantially purified gene product of HIV. Such gene products include those products encoded by the gag genes (p55, p39, p24, p17 and p15), the pol genes (p66/p51 and p31–34) and the transmembrane glycoprotein gp41. These gene products may be used alone or in combination with other HIV antigens.

The substantially purified gene product of HIV can be a substantially purified HIV p24 antigen. p24 can be substantially purified from the virus by biochemical methods known in the art, or can be produced by cloning and expressing the appropriate gene in a host organism such as bacterial, fungal or mammalian cells, by methods well known in the art. Alternatively, p24 antigen, or a modification or fragment thereof that retains the immunological activity of p24, can be synthesized, using methods well known in the art, such as automated peptide synthesis. Determination of whether a modification or fragment of p24 retains the immunological activity of p24 can be made, for example, by immunizing a mammal and comparing the immune responses so generated, or testing the ability of the modification or fragment to compete with p24 for binding to a p24 antibody.

The immunogenic compositions of the invention also contain an isolated nucleic acid molecule having at least one immunostimulatory sequence (ISS). The HIV antigen and the nucleic acid molecule can be mixed together, or can be conjugated by either a covalent or non-covalent linkage. Methods of conjugating antigens and nucleic acid molecules are known in the art, and exemplary methods are described in PCT publication WO 98/55495.

A nucleic acid molecule containing an ISS can be prepared using methods well known in the art including, for example, oligonucleotide synthesis, PCR, enzymatic or chemical degradation of larger nucleic acid molecules, and conventional polynucleotide isolation procedures. Methods of producing a nucleic acid molecule containing an ISS, including a nucleic acid molecule containing one or more modified bases or linkages, are described, for example, in PCT publication WO 98/55495.

Those skilled in the art can readily determine whether a particular nucleic acid molecule containing an ISS is effective in enhancing a desired immune response in a particular mammal by immunizing a mammal of the same species, or a species known in the art to exhibit similar immune responses, with a composition containing a particular ISS. For example, an optimal ISS to include in an immunogenic composition for administration to a human can be determined in either a human or a non-human primate, such as a baboon, chimpanzee, macaque or monkey.

The immunogenic compositions of the invention further contain an adjuvant, such as an adjuvant demonstrated to be safe in humans. An exemplary adjuvant is Incomplete Freund's Adjuvant (IFA). Another exemplary adjuvant contains mycobacterium cell wall components and monophosphoryl lipid A, such as the commercially available adjuvant DETOX™. Another exemplary adjuvant is alum. The preparation and formulation of adjuvants in immunogenic compositions are well known in the art.

Optionally, the immunogenic compositions of the invention can contain or be formulated together with other pharmaceutically acceptable ingredients, including sterile water or physiologically buffered saline. A pharmaceutically acceptable ingredient can be any compound that acts, for example, to stabilize, solubilize, emulsify, buffer or maintain sterility of the immunogenic composition, which is compatible with administration to a mammal and does not render the immunogenic composition ineffective for its intended purpose. Such ingredients and their uses are well known in the art.

The invention also provides kits containing an HIV antigen, an isolated nucleic acid molecule containing an ISS, and an adjuvant. The components of the kit, when combined, produce an immunogenic composition which enhances β-chemokine levels in a mammal.

The components of the kit can be combined ex vivo to produce an immunogenic composition containing an HIV antigen, a nucleic acid molecule containing an ISS and an adjuvant. Alternatively, any two components can be combined ex vivo, and administered with a third component, such that an immunogenic composition forms in vivo. For example, an HIV antigen can be emulsified in, dissolved in, mixed with, or adsorbed to an adjuvant and injected into a mammal, preceded or followed by injection of the nucleic acid molecule containing the ISS. Likewise, each component of the kit can be administered separately. Those skilled in the art understand that there are various methods of combining and administering an HIV antigen, an isolated nucleic acid molecule containing an ISS, and an adjuvant, so as to enhance β-chemokine production in a mammal.

An immunogenic composition of the invention is effective in enhancing β-chemokine production in a mammal administered the composition. As described in Examples I and III, below, production of the β-chemokine RANTES can be detected and quantitated using an ELISA assay of supernatants of T cells (such as lymph nodes cells or peripheral blood cells) from mammals administered the composition. In order to determine antigen-specific β-chemokine production, T cells from an immunized mammal can be stimulated with HIV antigen in combination with antigen-presenting thymocytes, and the β-chemokine levels measured in the supernatant. In order to determine non-specific β-chemokine production, either T cell supernatant or a blood or plasma sample from an immunized mammal can be assayed. Similarly, production of other β-chemokines, such as MIP-1α and MIP-1β, can be detected and quantitated using commercially available ELISA assays, according to manufacturer's instructions.

An immunogenic composition of the invention can further be capable of enhancing HIV-specific IgG2b antibody production in a mammal administered the composition. As described in Examples II and III, below, HIV in combination with ISS, or with IFA, stimulate HIV-specific IgG1 antibody production, but not HIV-specific IgG2b antibody production. In contrast, the immunogenic compositions of the invention can stimulate potent HIV-specific IgG2b antibody production. High levels of IgG2b antibodies, which are associated with a Th1 type response, are correlated with protection against HIV infection and progression to AIDS.

An immunogenic, composition of the invention can further be capable of enhancing HIV-specific cytotoxic T lymphocyte (CTL) responses in a mammal administered the composition. As described in Example II, below, an HIV antigen in combination with an adjuvant elicited low levels of IFN-γ production by either CD4+ T cells or CD8+ T cells. However, when an ISS was included in the composition together with an HIV and an adjuvant, there was a dose-dependent increase in IFN-γ production by both CD4+ T cells and CD8+ T cells.

IFN-γ production by CD4+ T cells is characterized as a classic Th1-type response. IFN-γ production by CD8+ T cells, however, is considered to be a cytotoxic T lymphocyte (CTL) response, and is highly correlated with cytolytic activity. CTL activity is an important component of an effective prophylactic or therapeutic anti-HIV immune response. Methods of determining whether a CTL response is enhanced following administration of an immunogenic composition of the invention are well known in the art, and include cytolytic assays (described, for example, in Deml et al. *supra* (1999)), and ELISA and ELISPOT assays for CD8-specific IFN-γ production (see Examples I and II, below).

The invention also provides a method of immunizing an individual. The method consists of enhancing β-chemokine production in an individual by administering to a mammal an immunogenic composition containing an HIV antigen, an isolated nucleic acid molecule containing an ISS, and an adjuvant. The components of the immunogenic composition can be administered in any order or combination, such that the immunogenic composition is formed ex vivo or in vivo.

Preferably, the HIV antigen, ISS and adjuvant are administered simultaneously or at about the same time, in about the same site. However, administering the components within several minutes or several hours of each other can also be effective in providing an immunogenic composition that enhances β-chemokine production. Additionally, administering the components at different sites in the mammal can also be effective in providing an immunogenic composition that enhances β-chemokine production.

The immunogenic compositions of the invention can be administered to a human to inhibit AIDS, such as by preventing initial infection of an individual exposed to HIV, reducing viral burden in an individual infected with HIV, prolonging the asymptomatic phase of HIV infection, increasing overall health or quality of life in an individual with AIDS, or prolonging life expectency of an individual with AIDS. As described in Examples I–III, below, administration to a mammal of an immunogenic composition containing an HIV antigen, an isolated nucleic acid molecule containing an immunostimulatory sequence, and an adjuvant stimulates immune responses correlated with protection against HIV infection and progression to AIDS.

In particular, the immunogenic compositions enhance β-chemokine production more effectively than would be expected by combination of any two components of the immunogenic compositions. Additionally, the immunogenic compositions promote strong Th1 type immune responses, including both Th1 type cytokines (e.g. IFN-γ) and Th1 type antibody isotypes (e.g. IgG2b). Thus, the immunogenic compositions of the invention will be effective as vaccines to prevent HIV infection when administered to seronegative individuals, and to reduce viral burden, prolong the asymptomatic phase of infection, and positively affect the health or lifespan of a seropositive individual.

Individuals who have been exposed to the HIV virus usually express in their serum certain antibodies specific for HIV. Such individuals are termed "seropositive" for HIV, in contrast to individuals who are "seronegative." The presence of HIV specific antibodies can be determined by commercially available assay systems.

At the present time, serological tests to detect the presence of antibodies to the virus are the most widely used method of determining infection. Such methods can, however, result in both false negatives, as where an individual has contracted the virus but not yet mounted an immune response, and in false positives, as where a fetus may acquire the antibodies, but not the virus from the mother. Where serological tests provide an indication of infection, it may be necessary to consider all those who test seropositive as in fact, being infected. Further, certain of those individuals who are found to be seronegative may in fact be treated as being infected if certain other indications of infection, such as contact with a known carrier, are satisfied.

The immunogenic compositions of the invention can be administered to an individual who is HIV seronegative or seropositive. In a seropositive individual, it may be desirable to administer the composition as part of a treatment regimen that includes treatment with anti-viral agents, such as protease inhibitors. Anti-viral agents and their uses in treatment regimens are well known in the art, and an appropriate regimen for a particular individual can be determined by a skilled clinician.

As shown in Example IV, below, administration of the immunogenic compositions of the invention to a primate fetus or to a primate neonate resulted in the generation of a strong anti-HIV immune response, indicating that the immune systems of fetuses and infants are capable of mounting an immune response to such compositions which should protect the child from HIV infection or progression to AIDS. Accordingly, the immunogenic compositions of the invention can be administered to an HIV-infected pregnant mother to prevent HIV transmission to the fetus, or to a fetus, an infant, a child or an adult as either a prophylactic or therapeutic vaccine.

The dose of the immunogenic composition, or components thereof, to be administered in the methods of the invention is selected so as to be effective in stimulating the desired immune responses. Generally, an immunogenic composition formulated for a single administration contains between about 1 to 200 μg of protein. Preferably, an immunogenic composition contains about 100 μg of protein for administration to a primate, such as a human. As shown in Example IV, below, about 100 μg of HIV antigen in an immunogenic composition elicits a strong immune response in a primate. As shown in Examples I–III, below, about 10 μg of HIV antigen is suitable for administration to a rodent.

The immunogenic composition can further contain from about 0.1 μg/ml to about 1 mg/ml of an isolated nucleic acid molecule containing an ISS sequence, such as about 1 μg/ml, about 10 μg/ml, or about 100 μg/ml. As shown in Example I, below, a ratio of at least 5:1 by weight of nucleic acid molecule to HIV antigen was more effective than lower ratios for eliciting immune responses. In rodents, an effective amount of an oligonucleotide containing an ISS in an immunogenic composition is from 5 μg to greater than 50 μg, such as about 100 μg. In primates, about 500 μg of an oligonucleotide containing an ISS is suitable in an immunogenic composition. Those skilled in the art can readily determine an appropriate amount of ISS to elicit a desired immune response.

As with all immunogenic compositions, the immunologically effective amounts of the components must be determined empirically, but can be based, for example, on immunologically effective amounts in animal models, such as rodents and non-human primates. Factors to be considered include the antigenicity, the formulation (e.g. volume, type of adjuvant), the route of administration, the number of immunizing doses to be administered, the physical condition, weight and age of the individual, and the like. Such factors are well known in the vaccine art and it is well within the skill of immunologists to make such determinations without undue experimentation.

The immunogenic compositions of the invention can be administered locally or systemically by any method known in the art, including, but not limited to, intramuscular, intradermal, intravenous, subcutaneous, intraperitoneal, intranasal, oral or other mucosal routes. The immunogenic compositions can be administered in a suitable, nontoxic pharmaceutical carrier, or can be formulated in microcapsules or as a sustained release implant. The immunogenic compositions of the invention can be administered multiple times, if desired, in order to sustain the desired immune response. The appropriate route, formulation and immunization schedule can be determined by those skilled in the art.

It is understood that modifications which do not substantially affect the activity of the various embodiments of this invention are also included within the definition of the invention provided herein. Accordingly, the following examples are intended to illustrate but not limit the present invention.

EXAMPLE I

Elicitation of Cytokine, Antibody and Chemokine Responses by HIV Immunogenic Compositions This example shows that immunogenic compositions containing an HIV antigen, an immunostimulatory nucleic acid molecule and an adjuvant, are potent stimulators of IFN-γ production (a Th1 cytokine), antibody responses and β-chemokine production in a mammal. In particular, β-chemokine production is enhanced to a greater extent than would be expected from the additive effects of any two components in the composition. Therefore, immunogenic compositions containing an HIV antigen, an immunostimulatory nucleic acid molecule and an adjuvant mediate potent immune responses of the types that are important in protecting against HIV infection and disease progression, indicating that these compositions will be effective prophylactic and therapeutic vaccines.

Materials and Methods

Oligodeoxynucleotides. ODN (oligodeoxynucleotides) used in this study were purchased from Retrogen (San Diego, Calif.). They were phosphorothioate-modified to increase resistance to nuclease degradation. The ODN sequences with the corresponding CpG or non-CpG motifs are underlined in Table 1.

TABLE 1

| ODN | Sequence | Motif | SEQ ID |
|---|---|---|---|
| 1826 | 5' TCCAT<u>GACGTT</u>CCT<u>GACGTT</u> 3' | CpG | 1 |
| Oct | 5' TGACTGTG<u>AACGTT</u>CG<u>AGATGA</u> 3' | CpG | 2 |
| 1745 | 5' TCCAAT<u>GAGCTT</u>CCT<u>GAGTCT</u> 3' | non-CpG | 3 |

Immunizations. The HIV-1 antigen was prepared from virus particles obtained from cultures of a chronically infected Hut 78 with a Zairian virus isolate (HZ321) which has been characterized as subtype "M," containing an env A/gag G recombinant virus (Choi et al., supra (1997)). The gp120 was depleted during the two-step purification process. The antigen was inactivated by the addition of β-propiolactone and gamma irradiation at 50 kGy. Western blot and HPLC analysis showed undetectable levels of gp120 in the preparation of this antigen (Prior et al., *Pharm. Tech.* 19:30–52 (1995)). For in vitro experiments, native p24 was preferentially lysed from purified HIV-1 antigen with 2% triton X-100 and then purified with Pharmacia Sepharose Fast Flow S resin. Chromatography was carried out at pH=5.0 and p24 was eluted with linear salt gradient. Purity of the final product was estimated to be >99% by both SDS (sodium dodecyl sulfate) electrophoresis and reverse phase high pressure liquid chromatography. The ODN was added to the diluted HIV-1 antigen in a volume of at least 5% of the final volume.

CFA (complete Freund's adjuvant) was prepared by resuspending mycobacterium tuberculosis H37RA (DIFCO, Detroit, Mich.) at 10 mg/ml in IFA (DIFCO, Detroit, Mich.). IFA or ISA 51® was formulated by adding one part of the surfactant Montanide 80 (high purity mannide monoleate, Seppie, Paris) to nine parts of Drakeol 6 VR light mineral oil (Panreco, Karnes City, Pa.). The gp120-depleted HIV-1 antigen was diluted in PBS to 200 μg/ml and emulsified with equal volumes of CFA or IFA with or without ODN.

Eight to twelve weeks old Lewis rats from Charles Rivers (Wilmington, Mass.), maintained in a pathogen-free facility, were injected intradermally in the hind footpad with 100 μl of emulsion. Each animal received 10 μg of the inactivated HIV-1 antigen in either CFA (n=6), IFA (n=6), 50 μg ISS (n=3), or IFA plus 50 μg ISS (n=6). Two weeks later, the animals were boosted subcutaneously in the base of the tail using the same regimen, except that the animals primed with HIV-1 antigen in CFA were instead boosted with HIV-1 antigen in IFA. Rats were primed and boosted with HIV-1 antigen in the presence of the ODN 1826, which contains an ISS, or ODN 1745, which does not contain an ISS. On day 28, the animals were sacrificed for cytokine, chemokine, and antibody analysis. For ISS dose response studies, n=3 for all groups. ELISA for antigen-specific antibody. Whole blood was collected from immunized animals by heart puncture at the end of the study. The SST tubes were centrifuged at 800 rpm for 20 minutes. Sera were aliquoted and stored at −20° C. until assayed. PVC plates (polychlorinated biphenyl plates, Falcon, Oxnard, Calif.) were coated with native p24 diluted in PBS at 1 μg/ml and stored at 4° C. overnight. Plates were blocked by adding 200 μl per well of 4% BSA in PBS for 1 hour. Sera were diluted in 1% BSA in PBS at 1:100 followed by four-fold serial dilution. 100 μl of diluted sera were added in duplicate and incubated at room temperature for 2 hours. Plates were washed with 0.05%. Tween 20 in PBS three times and blotted dry. The detecting secondary antibodies (goat anti-rat IgG biotin, goat anti-rat IgG1 biotin or goat anti-rat IgG2a biotin, Zymed, San Francisco, Calif.) were diluted in 1% BSA in PBS. 100 μl of diluted secondary antibody was added to each well and incubated at room temperature for another hour. After washing excess secondary antibody, strep-avidin-biotin-HRP (Pierce, Rockford, Ill.) were added at 50 μl per well and incubated for 30 minutes. Plates were washed with 0.05% Tween 20 in PBS three times. ABTS substrate (KPL, Gaithersburg, Md.) was added until a bluish-green color developed. The reaction was stopped by the addition of 1% SDS and the plate was read at absorbance 405 nm.

The antibody response reported as 50% antibody titer was the reciprocal of the dilution equal to 50% of the maximum binding (highest optical reading) for every given sample. The absorbance value (OD @ 405 nm) was plotted against antibody dilution in a log scale, yielding a sigmoidal dose response curve. 50% of the maximum binding was calculated by multiplying the highest OD by 0.5. The 50% value was located on the curve and the corresponding x-axis value was reported as the antibody dilution.

ELISA Assay for Cytokine and Chemokine Anaylsis. The draining lymph nodes (superficial inguinal and popliteal) were isolated from immunized animals two weeks after the boost. Single cell suspensions from these lymph nodes were prepared by mechanical dissociation using sterile 70 μm mesh screen. T cells were purified from lymph node cells by the panning method. Briefly, petri dishes (100×15 mm) were pre-coated with 20 μg/ml of rabbit anti-rat IgG (Rockland, San Francisco, Calif.) for 45 minutes at room temperature. The; petri dishes were washed twice with ice cold PBS and once with ice cold 2% human AB serum in PBS. $1 \times 10^7$ lymph node cells were added to pre-washed plates and incubated at 4° C. for 90 minutes. The non-adherent cells (enriched T cells) were then collected and transferred into sterile 50-ml conical tubes. The plates were washed twice and combined with the non-adherent cells. The cells were then centrifuged and cell pellets resuspended in complete media at $4 \times 10^6$ cells/ml (5% human AB serum in RPMI 1640, with 25 mM hepes, 2 mM L-glutamine, 100 μg streptomycin and $5 \times 10^{-6}$ M β-mercaptoethanol).

Gamma-irradiated thymocytes from a naive Lewis rat were used as antigen presenting cells. $2 \times 10^5$ enriched T cells and $5 \times 10^5$ thymocytes were added to each well of a 96-round bottom plate. The HIV-1 antigen and native p24 were diluted in complete media at 10 μg/ml while con A was diluted to 5 μg/ml. 100 μl of each antigen or T cell mitogen were added in triplicates. The plates were incubated at 5% $CO_2$, 37° C. for 72 hours. Supernatants were harvested and stored at −70° C. until assayed. The samples were assayed for IL-4, IFN-γ and RANTES using commercially available kits (Biosource, Camarillo, Calif.) specific for rat cytokines and chemokines.

Statistical methods. The Mann-Whitney U nonparametric statistic was utilized to compare groups. All p values are two tailed.

Results

As shown in FIG. 1A, administration of envelope-depleted HIV-1 in combination with IFA and ISS (ODN 1826) was a more potent inducer of both HIV-1 antigen-stimulated and p24 antigen-stimulated IFN-γ production than HIV-1 in CFA (p=0.002), HIV-1 in IFA, or HIV-1 in ISS (p=0.02). Increased production of unstimulated IFN-γ (control) was also observed following administration of envelope-depleted HIV-1 in combination with IFA and ISS. Unexpectedly, administration of HIV-1 in combination with IFA and ISS resulted in IFN-γ production that was several times greater than the additive effects of HIV-1 in IFA alone or HIV-1 in ISS alone. Of note, the level of cytokine secreted after HIV-1 stimulation was higher than after p24 stimulation, due to the presence of multiple T cell epitopes in the whole HIV-1 antigen.

Complete Freund's Adjuvant (CFA) is currently the most potent adjuvant known for stimulating cell-mediated immune responses. However, CFA is not an appropriate adjuvant for use in humans because of safety issues. As shown in FIG. 1A, HIV in CFA induced unstimulated and HIV-stimulated IFN-γ production more effectively than HIV in IFA alone or HIV in ISS alone, but not as well as HIV in the combination of IFA and ISS. Thus, the discovery of the superior effects of the combination of ISS and IFA for use in an HIV immunogenic composition provides for safe and effective vaccines for human therapy.

Figure 1B:
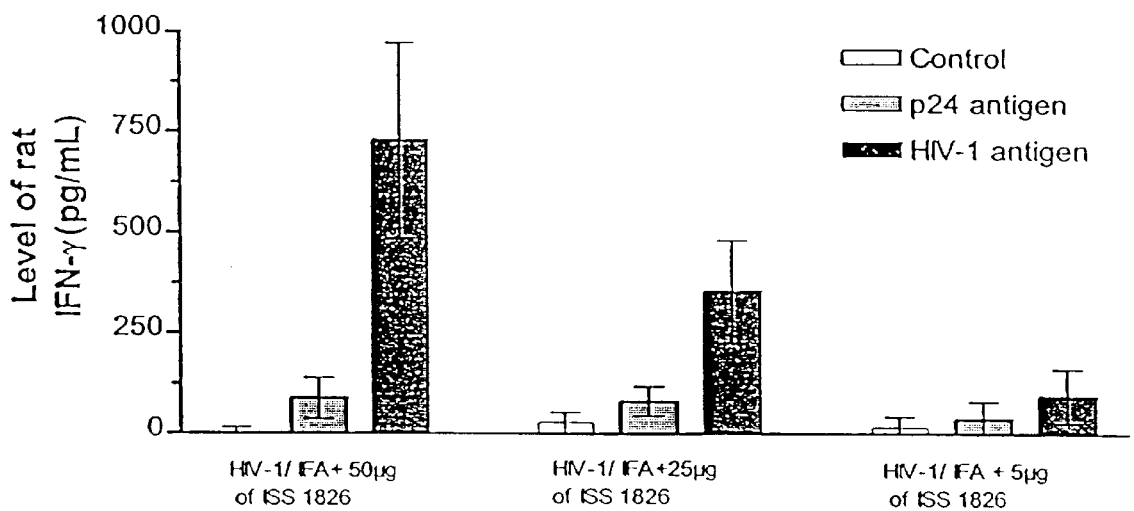

To examine the dose-related immune response to IFN-γ, Lewis rats were immunized with the inactivated gp120-depleted HIV-1 antigen emulsified in IFA containing different concentrations of CpG ODN 1826 (50, 25 and 5 μg per rat). The highest production of antigen-stimulated IFN-γ was obtained using 50 μg of CpG ODN 1826, as shown in FIG. 1B.

Figure 2A:
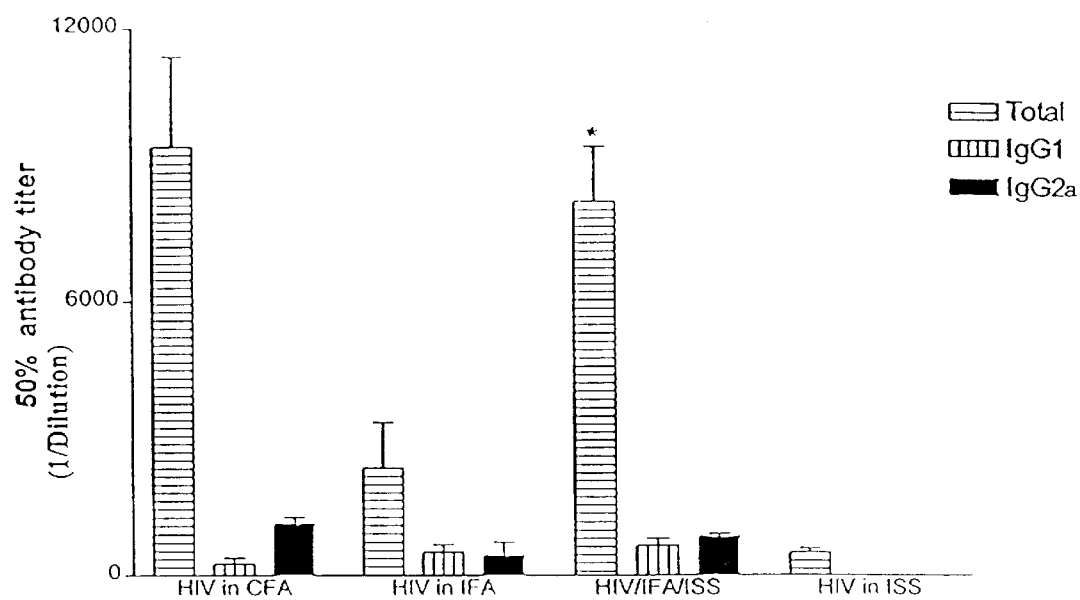
FIGS. 2A and 2B show production of total IgG, IgG1 and IgG2 isotypes for indicated treatment groups.
Figure 2B:
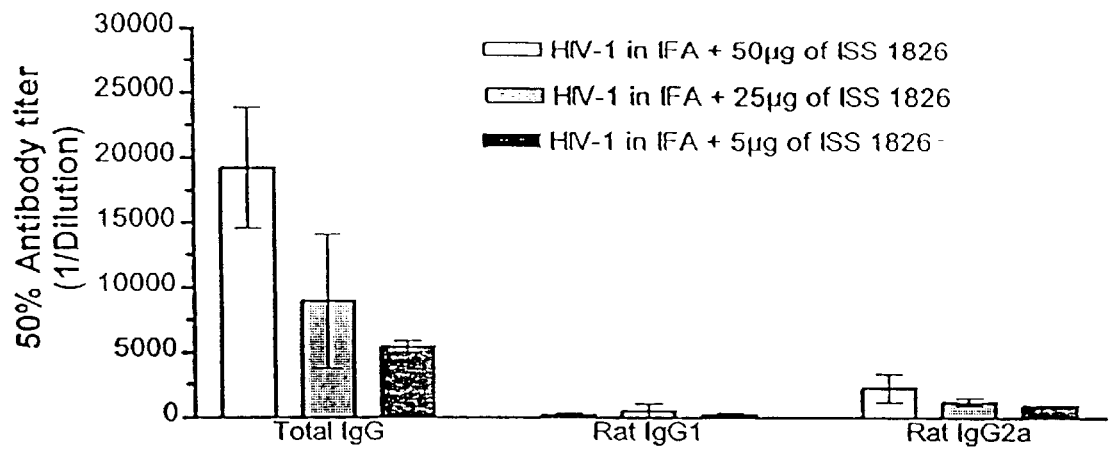

To examine whether CpG ODN could also boost the antibody response to an HIV-1 antigen, sera were assayed for total IgG and Th2 isotype (IgG1 and IgG2a) antibody responses to p24 antigen. As shown in FIG. 2A, anti-p24 total IgG responses were strongly enhanced and comparable in both the HIV in CFA and HIV in IFA/ISS groups of animals. Administration of HIV-1 in combination with IFA and ISS resulted in total p24 antibody production that was greater than the additive effects of HIV-1 in IFA alone or ISS alone, and almost as great as HIV-1 in CFA. The IgG1 and IgG2a responses were comparable among animals immunized with HIV-1 antigen in CFA, IFA or IFA/ISS. As shown in FIG. 2B, the antibody response was dependent on the dose of ISS.

Figure 3A:
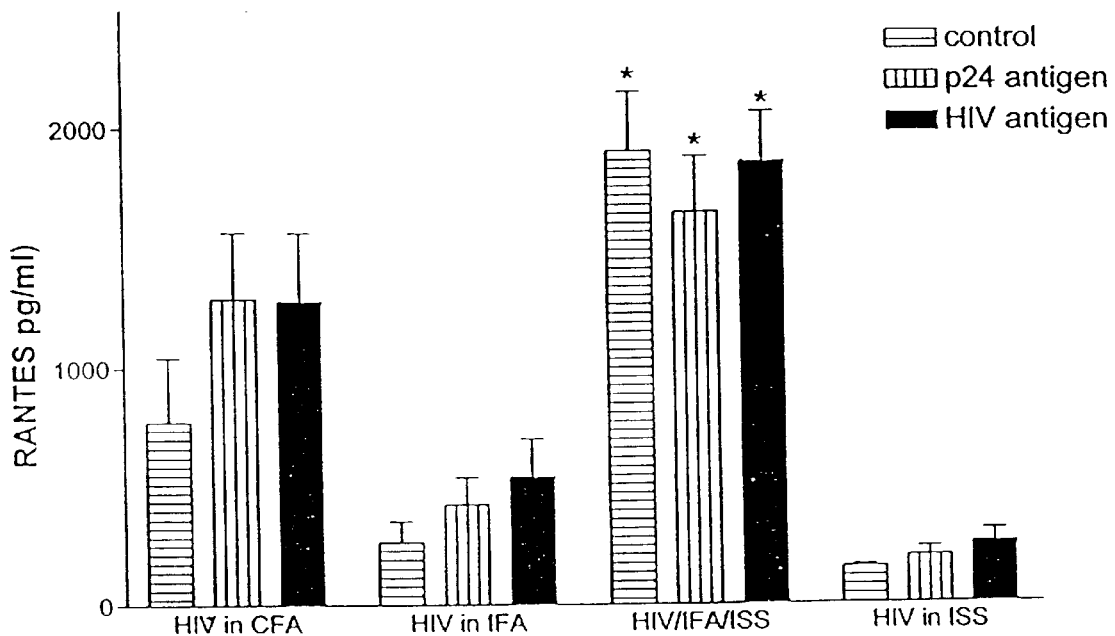
FIGS. 3A and 3B show control and antigen-stimulated RANTES production for indicated treatment groups.
Figure 3B:
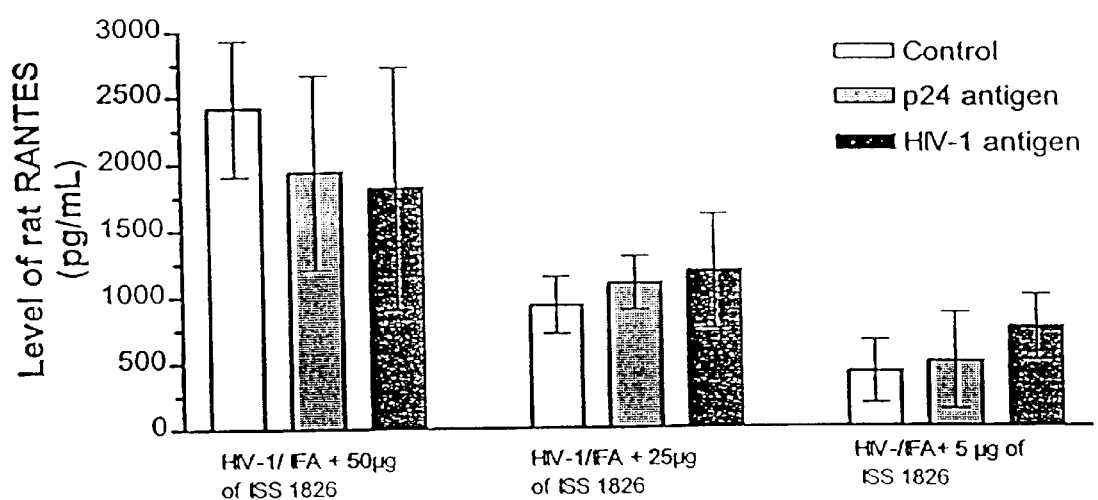

Production of the β-chemokine RANTES in response to immunization was then examined. As shown in FIG. 3A, both unstimulated and antigen-stimulated cells from the HIV/IFA/ISS group showed enhanced production of RANTES, to a level comparable with the HIV in CFA group, and significantly higher than the HIV/IFA group (p=0.002) or HIV/ISS group (p=0.02). Unexpectedly, administration of HIV-1 in combination with IFA and ISS resulted in both unstimulated and antigen-stimulated RANTES production that was greater than the additive effects of HIV-1 in IFA alone or HIV-1 in ISS alone. As shown in FIG. 3B, both unstimulated and antigen-stimulated RANTES production was dependent on the dose of ISS.

In none of the groups was production observed of antigen-induced IL-4, a Th2 type cytokine. The control sequence (1745) did not stimulate IFN-γ, RANTES, or p24 antibody.

Figure 4A:
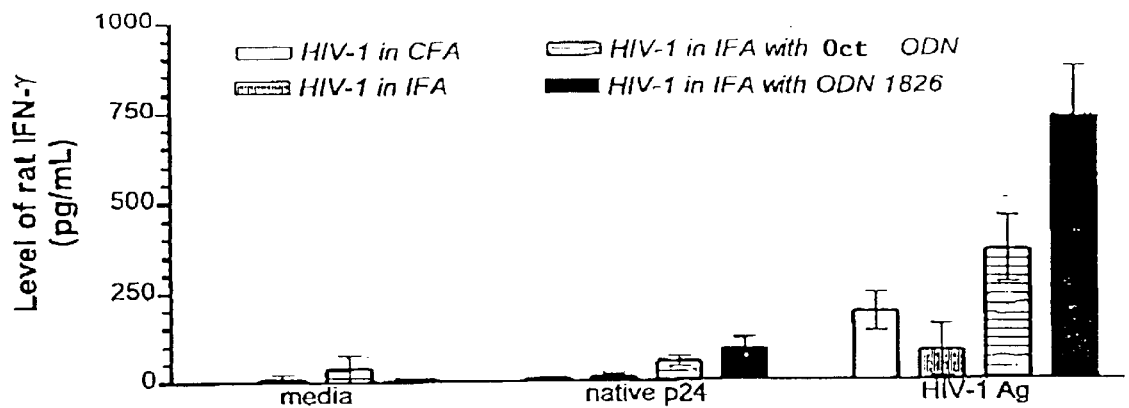
FIG. 4A shows a comparison of IFN-γ production following treatment with two different immunostimulatory sequences.
Figure 4B:
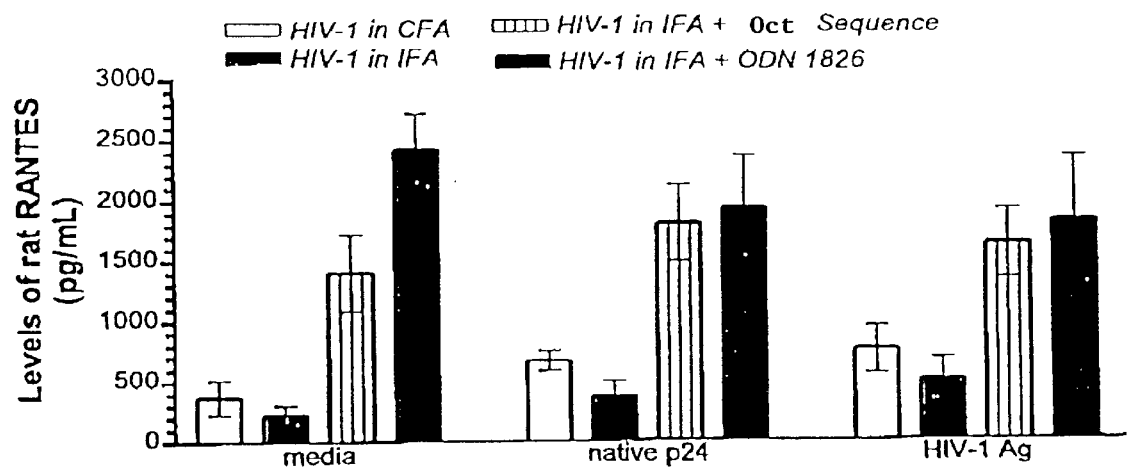
FIG. 4B shows a comparison of IFN-γ production following treatment with two different immunostimulatory sequences.

Cytokine and chemokine production was compared with compositions containing two oligonucleotides containing different immunostimulatory sequences. As shown in FIG. 4A, immunogenic compositions containing HIV-1 antigen and IFA with either ODN 1826 (SEQ ID NO:1) or ODN Oct (SEQ ID NO:2) induced antigen-stimulated IFN-γ production to a greater extent than compositions containing HIV-1 antigen and IFA, or HIV-1 antigen and CFA. Furthermore, as shown in FIG. 4B, immunogenic compositions containing HIV-1 antigen and IFA with either ODN Oct or ODN 1826 induced unstimulated and antigen-stimulated RANTES production to a greater extent than compositions containing HIV-1 antigen and IFA, or HIV-1 antigen and CFA.

Thus, the immunogenic compositions of the invention can be used to enhance β-chemokine production in an individual. Because of the strong correlation between β-chemokine levels and protection from HIV infection and disease progression, the compositions of the invention will be more effective than other described compositions for inhibiting AIDS.

EXAMPLE II

Elicitation of CD4 and CD8 Immune Responses by HIV Immunogenic Compositions

This example shows the induction of potent CD4 and CD8 HIV-specific Th1 type immune responses following immunization with an immunogenic composition containing an HIV antigen, a nucleic acid containing an immunostimulatory sequence and an adjuvant. Antigen-specific responses by CD8+, cytotoxic T lymphocytes are an important factor in preventing initial HIV infection and disease progression. Thus, this example provides further evidence that the immunogenic compositions of the invention are effective prophylactic and therapeutic vaccines.

Materials and Methods

HIV antigen, ISS (ODN 1826) and IFA were prepared essentially as described in Example I. Lewis rats were immunized essentially as described in Example I, and sacrificed at day 28 for ELISPOT and p24 antibody analysis. p24 antibody analysis was performed essentially as described in Example I.

ELISPOT for gamma-interferon from bulk and purified T cell populations. Single cell suspensions were prepared from spleens of the immunized rats by mincing and pressing through a sterile fine mesh nylon screen in RPMI 1640 (Hyclone, Logan, Utah). The splenocytes were purified by ficoll gradient centrifugation. CD4 and CD8 cells were isolated by magnetic bead depletion. $2 \times 10^7$ cells were stained with 5 μg of either mouse anti-rat CD4 (clone: OX-35, Pharmingen, San Diego, Calif.) or mouse anti-rat CD8 (clone: OX-8, Pharmingen, San Diego, Calif.). Cells were incubated on ice for 30 minutes and washed with ice cold 2% Human AB serum in PBS. Pre-washed Dynabeads (DYNAL, Oslo, Norway) coated with goat anti-mouse IgG were added to the cell suspension and incubated at 4° C. for 20 minutes with constant mixing.

Purified CD4, CD8 and non-depleted splenocytes were resuspended in complete media (5% inactivated Human AB serum in RPMI 1640, Pen-strep, L-glutamine and β-ME) at $5 \times 10^6$ cells/ml and used for ELISPOT assay to enumerate the individual IFN-γ secreting cells. Briefly, 96 well nitrocellulose bottom microtiter plates (Millipore Co., Bedford, U.K.) were coated with 400 ngs per well of mouse anti-rat IFN-γ (clone: DB-1, Biosource, Camarillo, Calif.). After overnight incubation at 4° C., plates were washed with sterile PBS and blocked with 5% human AB serum in RPMI 1640 containing pen-strep, L-glutamine and β-ME) for 1 hour at room temperature. Plates were washed with sterile PBS and $5 \times 10^5$ per well of splenocytes (purified CD4, purified CD8 or non-depleted) were added in triplicate and incubated overnight at 37° C. and 5% $CO_2$. Cells were cultured with media, OVA (Chicken Egg Ovalbumin, Sigma-Aldrich, St. Louis, Mo.), native p24 or gp120-depleted HIV-1 antigen. CD4 purified and CD8 purified splenocytes were assayed in complete media containing 20 units/ml of recombinant rat IL-2 (Pharmingen, San Diego, Calif.).

After washing unbound cells, 400 ng per well of the polyclonal rabbit anti-rat IFN-γ were added and incubated at room temperature for 2 hours, then washed and stained with goat anti rabbit IgG biotin (Zymed, San Francisco, Calif.). After extensive washes with sterile PBS, avidin alkaline phosphatase complex (Sigma-Aldrich, St. Louis, Mo.) was added and incubated for another hour at room temperature. The spots were developed by adding chromogenic alkaline phosphate substrate (Sigma, St. Louis, Mo.) and the IFN-γ cells were counted using a dissection microscope (×40) with a highlight 3000 light source (Olympus, Lake Success, N.Y.).

Statistical Methods. The Mann-Whitney U nonparametric statistic was utilized to compare groups. The Spearman rank correlation was performed to examine relationships between CD4 and CD8 gamma interferon production. All p values are two tailed.

Results

The production of IFN-γ by non-depleted splenocytes, and by purified CD4+ or purified CD8+ populations, was examined. IFN-γ production by CD4+ cells is a characteristic Th1 immune response, whereas IFN-γ production by CD8+ cells is a correlate of cytotoxic T lymphocyte (CTL) cytolytic activity.

Figure 5A:
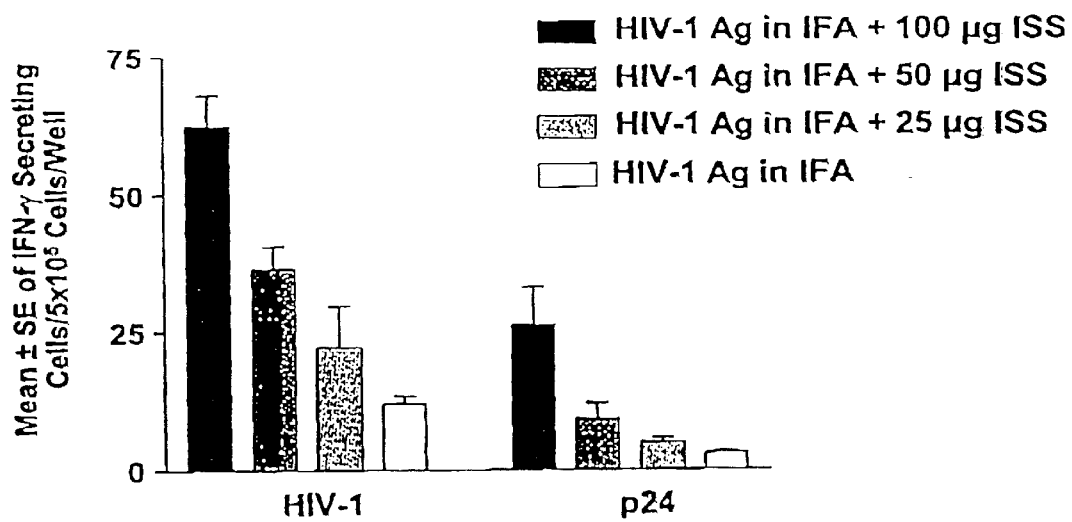
FIG. 5A shows HIV antigen-stimulated IFN-γ production from peripheral blood mononuclear cells.

The frequency of IFN-γ producing cells increased with dose of ISS in non-depleted splenocytes in response to either whole-killed, gp120-depleted HIV (the immunizing antigen) or purified p24 antigen (see FIG. 5A). The highest frequency of cytokine producing cells was observed with the combination of 100 μg of ISS with HIV-1 in IFA, for both HIV-1 and p24 antigen stimulated cells (p=0.03 when compared the HIV in IFA group).

Figure 5B:
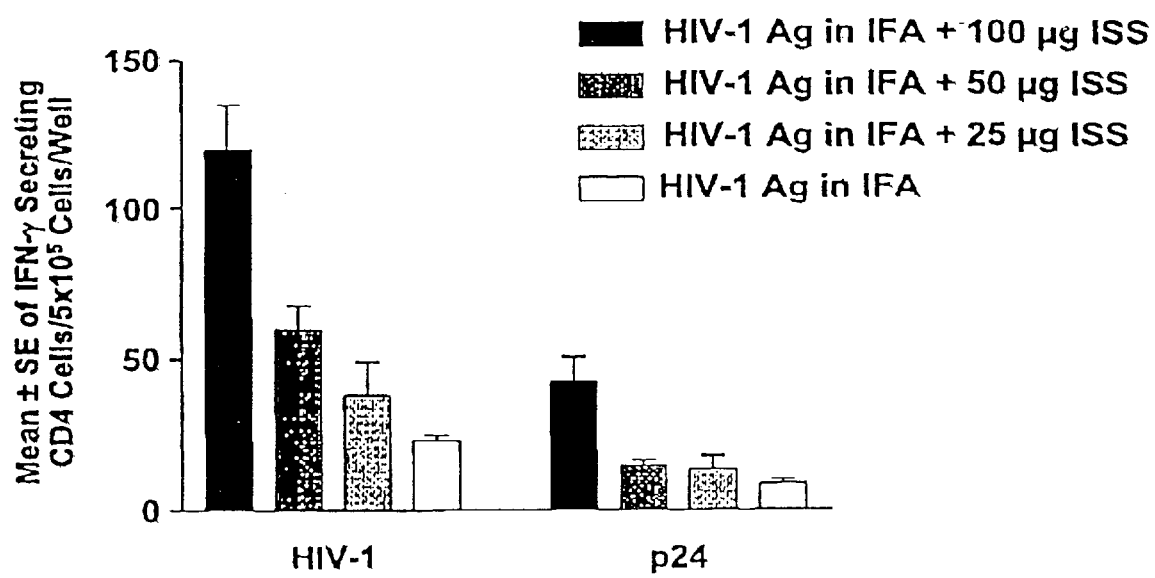
FIG. 5B shows HIV antigen-stimulated IFN-γ production from CD4+ cells.
Figure 5C:
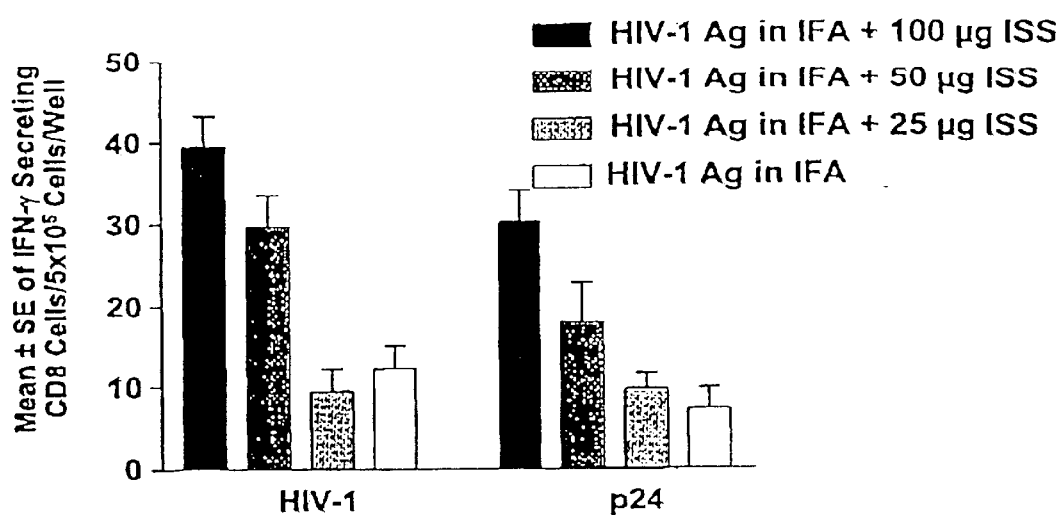
FIG. 5C shows HIV antigen-stimulated IFN-γ production from CD8+ cells.

The purified CD4+ T cell population also exhibited a dose-dependent increase in the frequency of cells expressing IFN-γ in response to HIV and p24 antigens, with the greatest frequency being at the 100 μg dose of ISS when combined with HIV-1 in IFA (p=0.03 when compared the HIV in IFA group)(see FIG. 5B). Furthermore, the purified CD8+ population also exhibited a dose-dependent increase in the frequency of cells expressing IFN-γ in response to HIV and p24 antigens, with the greatest frequency being at the 100 μg dose of ISS when combined with HIV-1 in IFA (p=0.03 when compared the HIV in IFA group)(see FIG. 5C). None of the animals produced IFN-γ secreting cells when stimulated with OVA, an irrelevant protein antigen.

Of note, the frequency of IFN-γ producing CD8+ T cells was generally lower than the frequency of CD4+ T cells expressing IFN-γ. There was a strong correlation between the generation of IFN-γ between CD4+ T cells and CD8+ T cells with both HIV antigen stimulation (r=0.80, p=0.002) and for p24 antigen stimulation (r=0.79, p=0.003).

The results shown in FIGS. 5A, B and C thus demonstrate that the immunogenic compositions of the invention elicit Th1 and cytotoxic T lymphocyte responses, both of which are correlated with protection from initial HIV infection and progression to AIDS.

Figure 6A:
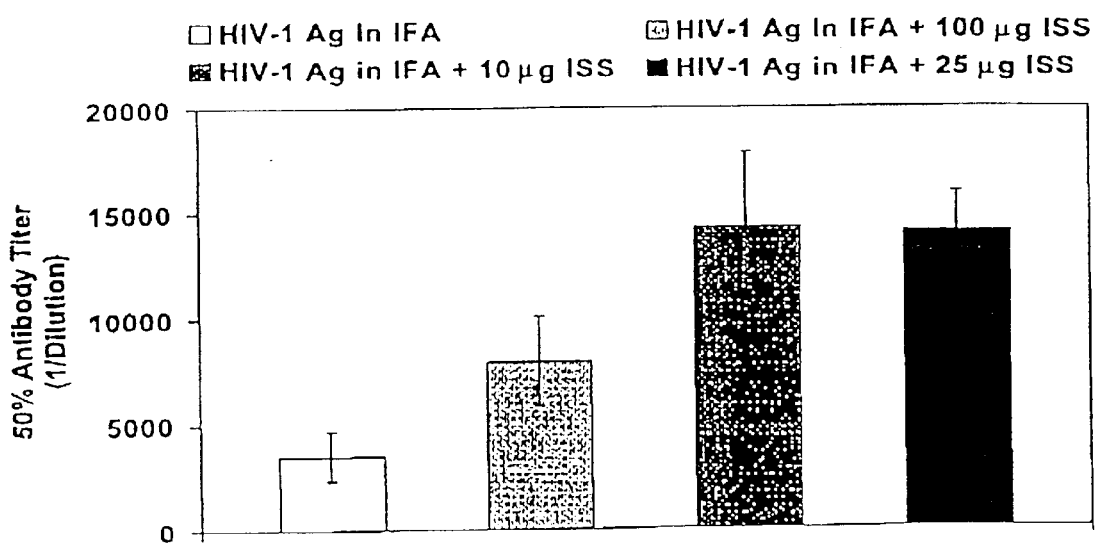
FIG. 6A shows production of total anti-p24 IgG for indicated treatment groups.
Figure 6B:
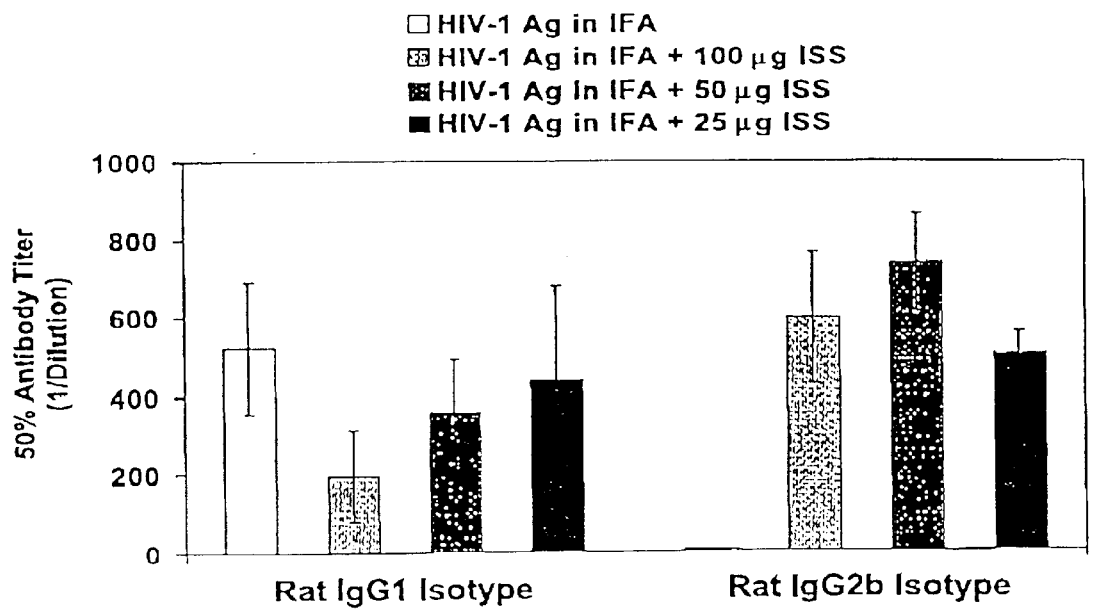
FIG. 6B shows production of anti-p24 IgG1 and IgG2 isotypes for indicated treatment groups.

Finally, total IgG, IgG1 and IgG2b specific for p24 was examined. As shown in FIG. 6A, the addition of ISS at all doses to HIV in IFA increased anti-p24 antibody response (total IgG) compared to HIV in IFA, although a dose response was not evident. Specifically, the addition of ISS to HIV in IFA favored the production of IgG2b antibody (a Th1 type response) compared to HIV in IFA, which induced only IgG1 subtype antibody (a Th2 type response), as shown in FIG. 6B.

In summary, the data in this Example show that an immunogenic composition containing an HIV antigen, an ISS and an adjuvant can be used to generate potent HIV-specific CD4 and CD8 HIV-specific immune responses. The induction of CD4 T helper cells may be pivotal for generation of CD8 effector cells. CD8 T cells can serve as effectors against HIV virus by several mechanisms, including direct cytolytic (CTL) activity, as well as through the release of antiviral suppressive factors, such as β-chemokines and other less well-characterized factors. These results contrast with results reported by Deml et al., *supra* (1999), who showed that a combination of HIV envelope gp160 antigen, an ISS and an adjuvant did not induce HIV-specific CTL activity. Accordingly, the compositions described herein are superior to other described compositions for use as HIV vaccines.

EXAMPLE III

Comparison of Immune Responses Elicited by Different Immunogenic Compositions and Immunization Schedules This example shows that a nucleic acid containing an ISS is more effective in eliciting protective immune responses, including RANTES production and HIV-specific IgG2b antibody production, when administered simultaneously with an HIV antigen and an adjuvant than when used to prime the mammal one week prior to administration of the antigen and adjuvant. This example also shows that a composition containing an HIV antigen, an ISS and an adjuvant promotes antigen-dependent lymphocyte proliferation more effectively than a composition containing only HIV and IFA.

Materials and Methods

HIV antigen, ISS (ODN 1826) and IFA were prepared essentially as described in Example I. Lewis rats (three per group) were immunized at day 7 and, where indicated, primed at day 0, with the compositions shown in Table 2.

TABLE 2

| Group | Day 0 | Day 7 |
| --- | --- | --- |
| A | ISS | HIV-1 |
| B |  | HIV-1 |
| C | ISS | HIV-1/IFA |
| D |  | HIV-1/IFA |
| E |  | HIV-1/IFA/ISS |

Animals were sacrificed at day 21 for cytokine, chemokine and antibody analysis, essentially as described in Example I, as well as for analysis of lymphocyte proliferation.

Lymphocyte proliferation assay. Single cell suspensions were prepared from the draining lymph nodes of immunized animals. B cells were depleted from the lymph node cells by panning. Briefly, lymph node cells were incubated with anti-rat IgG pre-coated petri dishes for 90 minutes. The non-adherent cells (enriched T cells) were collected and resuspended in complete tissue culture media at $4 \times 10^6$ cells/ml. The enriched T cells were cultured with p24 or HIV-1 antigen in the presence of γ-irradiated thymocytes at 37° C., 5% $CO_2$ for 40–48 hours. Samples were pulsed with tritiated thymidine and incubated for another 16 hours. Cells were harvested and tritiated thymidine incorporation was counted using a β-scintillation counter.

Results

Figure 7A:
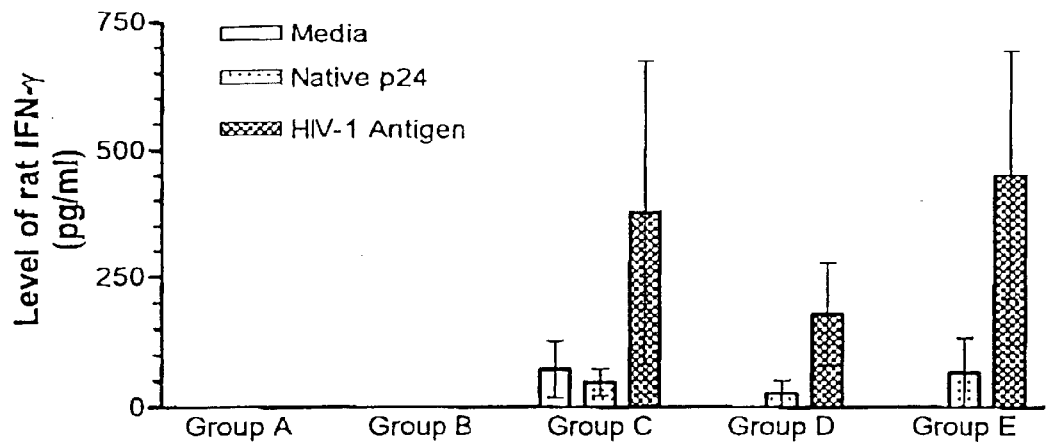
FIG. 7A shows control and antigen-stimulated IFN-γ production for different treatment groups.

As shown in FIG. 7A, T cells from animals primed with ISS and subsequently boosted with HIV-1 in IFA (Group C), animals immunized with HIV-1 in IFA, and animals immunized with a combination of HIV-1, IFA and ISS (Group E), exhibited increased IFN-γ production in response to whole-killed, gp120-depleted HIV (the immunizing antigen) and a lesser increase in IFN-γ production in response to purified p24 antigen.

Figure 7B:
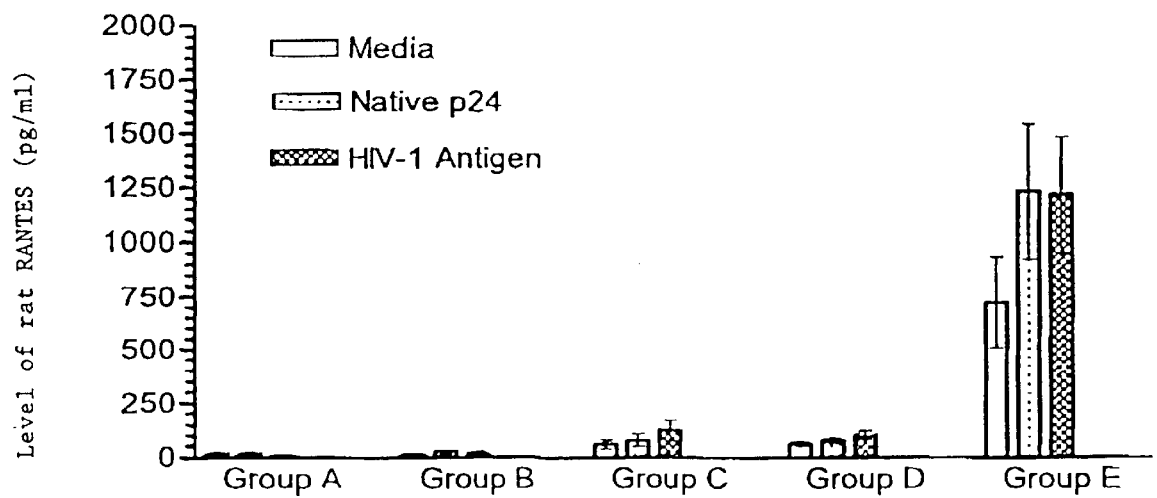
FIG. 7B shows control and antigen-stimulated RANTES production for different treatment groups.

However, as shown in FIG. 7B, only T cells from animals immunized with a combination of HIV-1, IFA and ISS (Group E) showed high levels of either non-stimulated (media), or HIV-stimulated RANTES production. RANTES production from animals of Group E was several fold higher than from animals primed with ISS, then boosted one week later with HIV-1 in IFA (Group C).

Figure 7C:
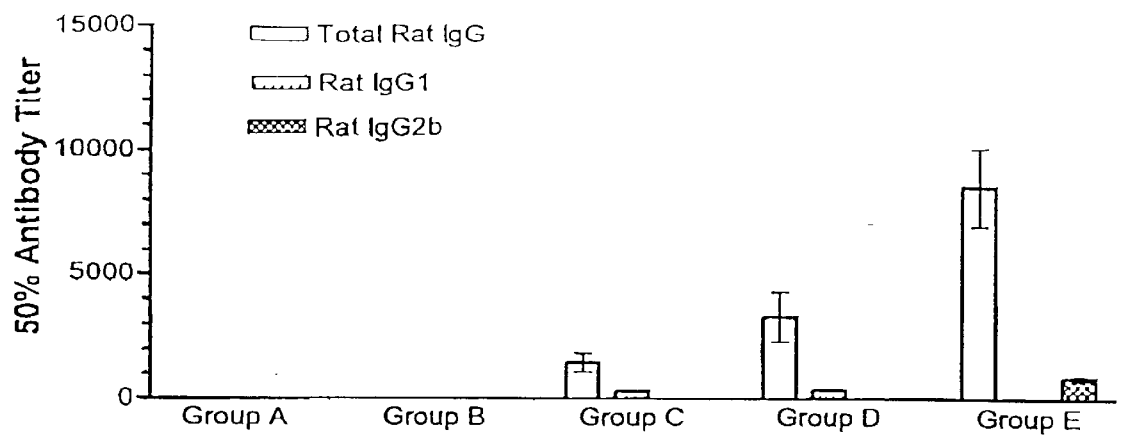
FIG. 7C shows production of total anti-p24 IgG for different treatment groups.
Figure 7D:
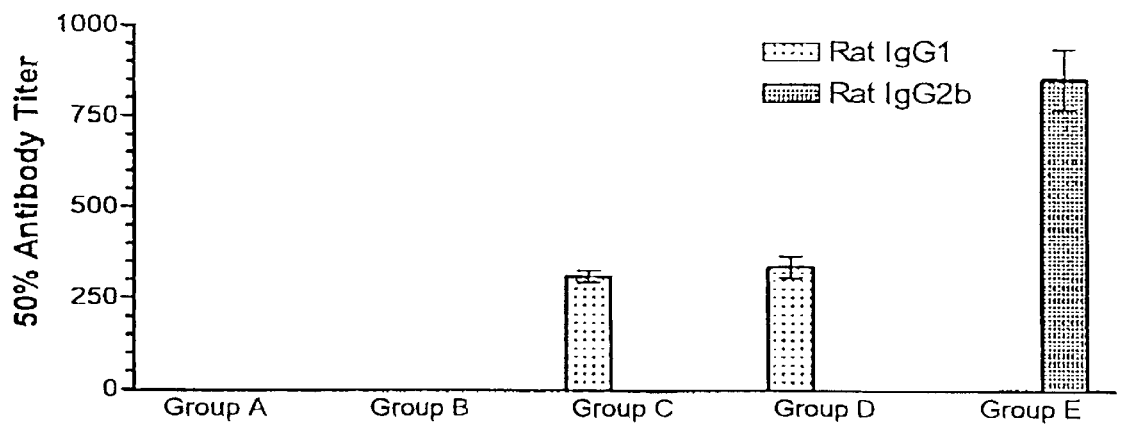
FIG. 7D shows production of anti-p24 IgG1 and IgG2 isotypes for different treatment groups.

Serum levels of total IgG, IgG1 and IgG2b specific for p24 antigen were also examined. As shown in FIG. 7C, animals immunized with a combination of HIV-1, IFA and ISS (Group E) showed the highest levels of total IgG. Unexpectedly, whereas animals not receiving ISS (Group D) and animals primed with ISS (Group C) produced primarily IgG1 (Th2-type) antibodies, animals immunized with a combination of HIV-1, IFA and ISS (Group E) produced primarily IgG2b (Th1-type) antibodies (see FIG. 7D).

Figure 7E:
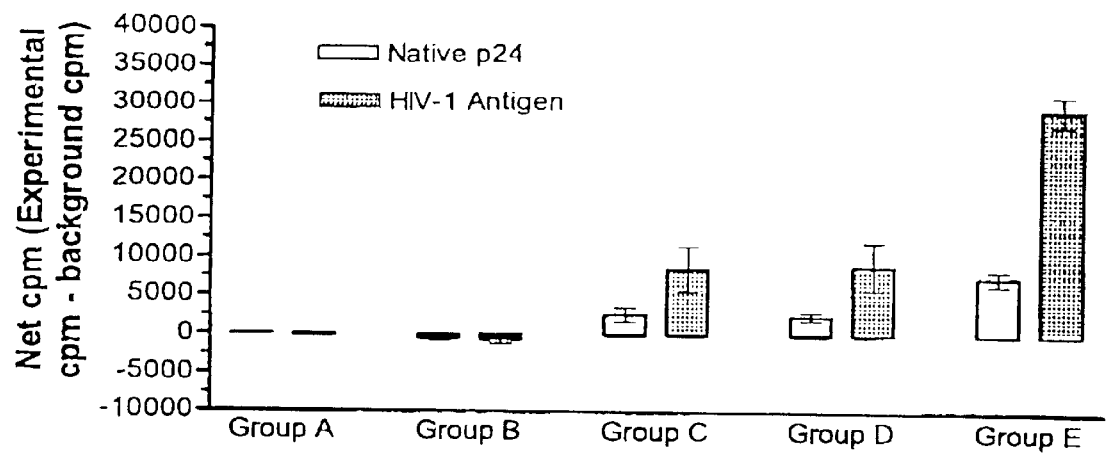
FIG. 7E shows T cell proliferative responses to HIV antigens for different treatment groups.

T cell proliferative responses to p24 antigen and gp120-depleted HIV were also measured. As shown in FIG. 7E, T cells from animals immunized with a combination of HIV-1, IFA and ISS (Group E) proliferated more strongly in response to either gp120-depleted HIV or p24 antigen than did T cells from animals primed with ISS then administered HIV-1 in IFA one week later (Group C), or from animals administered only HIV-1 in IFA (Group D).

Thus, the immunogenic compositions of the invention effectively elicit HIV-specific Th1 cytokine (IFN-γ) and humoral responses (IgG2 antibodies), and enhance both non-specific and HIV-specific β-chemokine production. These responses to the immunogenic compositions correlate with strong HIV-specific T lymphocyte proliferative responses.

EXAMPLE IV

Immunization of a Primate With an HIV Immunogenic Composition

This example shows that immunogenic compositions containing an HIV antigen, an isolated nucleic acid molecule containing an ISS and an adjuvant are effective in enhancing HIV-specific immune responses in primates.

Three baboon fetuses were injected in utero with an immunogenic composition containing gp120-depleted HIV-1 (100 μg total protein, equivalent to 10 p24 units) in IFA with 500 μg of the ISS designated ODN 2006. The sequence of ODN 2006 is 5'-TCGTCGCTGTTGTCGT TTCTT-3' (SEQ ID NO:4). Four weeks later, the fetuses were boosted using the same regimen.

Peripheral blood mononuclear cells from the neonatal baboons were collected, and proliferative responses to p24 and HIV-1 antigen were assayed. As shown in Table 3, in all three animals, the HIV-1 stimulation index, which is the ratio of T cell proliferation ($^3$H incorporation) in response to antigen to T cell proliferation without antigen, was indicative of a strong immune response (i.e. stimulation index >3). Two baboon fetuses injected in utero and boosted as neonates showed similar results.

TABLE 3

| Baboon | HIV-1 Stimulation Index |
|---|---|
| 6533 | 13.3 |
| 5924 | 5.87 |
| 6683 | 15.1 |

Production of HIV-specific antibodies, cytokines and β-chemokines are also measured in the same baboons. These results show that the types of immune responses elicited by the immunogenic compositions described in Examples I–III, above, for rodents, are also elicited in primates.

These results demonstrate that the HIV immunogenic compositions and methods of the invention are effective in primates in stimulating HIV-specific immune responses. Furthermore, these results demonstrate that fetuses and infants are able to elicit strong HIV immune responses to the immunogenic compositions of the invention, indicating that these compositions will be useful for preventing maternal transmission of HIV and as pediatric vaccines.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. An immunogenic composition, comprising:

(a) a whole-killed HIV virus devoid of outer envelope protein gp 120;

(b) an isolated nucleic acid molecule containing an immunostimulatory sequence (ISS); and (c) an adjuvant, wherein said composition synergistically enhances β-chemokine levels in a mammal.

2. The immunogenic composition of claim 1, wherein said HIV virus is HIV-1.

3. The immunogenic composition of claim 1, wherein said HIV virus is an HZ321 strain virus.

4. The immunogenic composition of claim 1, wherein said isolated nucleic acid molecule is an oligodeoxynucleotide.

5. The immunogenic composition of claim 1, wherein said isolated nucleic acid molecule comprises two or more CpG sequences.

6. The immunogenic composition of claim 1, wherein said isolated nucleic acid molecule comprises at least one sequence consisting of 5'-Cytosine, Guanine, Pyrimidine, Pyrimidine-3'.

7. The immunogenic composition of claim 1, wherein said isolated nucleic acid molecule comprises at least one sequence consisting of 5'-CGTT-3'.

8. The immunogenic composition of claim 1, wherein said isolated nucleic acid molecule comprises at least one sequence consisting of 5'-Purine, Purine, Cytosine, Guanine, Pyrimidine, Pyrimidine-3'.

9. The immunogenic composition of claim 1, wherein said isolated nucleic acid molecule comprises at least one sequence consisting of 5'-GACGTT-3'.

10. The immunogenic composition of claim 1, wherein said isolated nucleic acid molecule comprises at least one sequence consisting of 5'-TCCATGACGTTCCTGACGTT-3' (SEQ ID NO:1).

11. The immunogenic composition of claim 1, wherein said isolated nucleic acid molecule comprises at least one sequence consisting of 5'-AACGTTCG-3'.

12. The immunogenic composition of claim 1, wherein said isolated nucleic acid molecule comprises a phosphorothioate backbone.

13. The immunogenic composition of claim 1, wherein said HIV virus is conjugated to said nucleic acid molecule.

14. The immunogenic composition of claim 1, wherein said adjuvant is suitable for use in humans.

15. The immunogenic composition of claim 1, wherein said adjuvant comprises incomplete Freund's adjuvant (IFA).

16. The immunogenic composition of claim 1, wherein said adjuvant comprises mycobacterium cell wall components and monophosphoryl lipid A.

17. The immunogenic composition of claim 1, wherein said adjuvant comprises alum.

18. The immunogenic composition of claim 1, wherein said enhanced β-chemokine production is non-specific β-chemokine production.

19. The immunogenic composition of claim 1, wherein said enhanced β-chemokine production is HIV-specific β-chemokine production.

20. The immunogenic composition of claim 1, wherein said β-chemokine is RANTES.

21. The immunogenic composition of claim 1, said composition further capable of enhancing HIV-specific IgG2b antibody production in a mammal.

22. The immunogenic composition of claim 1, said composition further capable of enhancing an HIV-specific cytotoxic T lymphocyte (CTL) response in a mammal.

23. A kit, comprising:

(a) whole-killed HIV virus devoid of outer envelope protein gp120;

(b) an isolated nucleic acid molecule containing an immunostimulatory sequence (ISS); and (c) an adjuvant;

wherein at least one of said kit components is in a separate container from the other components and said kit components, when combined, produce the immunogenic composition of claim 1.

24. A method of making the immunogenic composition of claim 1, comprising combining:

(a) a whole-killed HIV virus devoid of outer envelope protein gp120;

(b) an isolated nucleic acid molecule containing an immunostimulatory sequence (ISS); and (c) an adjuvant.

* * * * *